(12) United States Patent
Messadek

(10) Patent No.: US 7,608,640 B2
(45) Date of Patent: Oct. 27, 2009

(54) GLYCINE BETAINE AND ITS USE

(76) Inventor: Jallal Messadek, Place des Beguinages 2, B-4000 Liege (BE)

( * ) Notice: Subject to any disclaimer, the term of this patent is extended or adjusted under 35 U.S.C. 154(b) by 928 days.

(21) Appl. No.: 10/635,048

(22) Filed: Aug. 4, 2003

(65) Prior Publication Data
US 2004/0033223 A1 Feb. 19, 2004

Related U.S. Application Data

(63) Continuation-in-part of application No. PCT/BE01/00222, filed on Dec. 21, 2001.

(51) Int. Cl.
*A01N 37/12* (2006.01)
(52) U.S. Cl. .................... 514/561; 514/165; 424/400; 424/422
(58) Field of Classification Search ............. 514/165
See application file for complete search history.

(56) References Cited

U.S. PATENT DOCUMENTS

| | | | |
|---|---|---|---|
| 4,066,756 A | 1/1978 | Orr et al. | |
| 4,605,548 A * | 8/1986 | Ushiyama et al. | 424/449 |
| 4,703,045 A | 10/1987 | Guinot | |
| 4,911,916 A * | 3/1990 | Cleary | 424/449 |
| 5,405,614 A * | 4/1995 | D'Angelo et al. | 424/449 |
| 5,716,941 A | 2/1998 | Rabinoff | |
| 5,814,599 A * | 9/1998 | Mitragotri et al. | 514/3 |
| 5,876,780 A | 3/1999 | Vertanen et al. | |
| 5,880,098 A | 3/1999 | Häussinger | |
| 5,928,195 A * | 7/1999 | Malamud et al. | 604/141 |
| 5,961,999 A | 10/1999 | Bimczok et al. | |
| 6,235,311 B1 | 5/2001 | Ullah et al. | |
| 6,287,765 B1 * | 9/2001 | Cubicciotti | 435/6 |
| 6,355,166 B1 | 3/2002 | Amarasinghe et al. | |
| 6,399,785 B1 * | 6/2002 | Murphy et al. | 548/417 |
| 6,476,006 B2 | 11/2002 | Flashner-Barak et al. | |
| 6,855,734 B2 * | 2/2005 | Messadek | 514/561 |
| 2002/0034757 A1 * | 3/2002 | Cubicciotti | 435/6 |
| 2002/0065320 A1 | 5/2002 | Messadek | |
| 2002/0183380 A1 | 12/2002 | Hunter | |
| 2006/0233877 A1 | 10/2006 | Messadek et al. | |

FOREIGN PATENT DOCUMENTS

| | | |
|---|---|---|
| BE | 1012546 | 12/2000 |
| BE | 09900164 | 12/2000 |
| BE | 1012712 | 2/2001 |
| BE | 2003/0248 | 4/2003 |
| DE | 19910682 | 9/2000 |
| EP | 0347864 | 6/1989 |
| EP | 0349902 | 6/1989 |
| EP | 0781554 | 7/1996 |
| FR | 2590 M | 3/1963 |
| FR | 2590 M | 6/1964 |
| FR | 70.47549 | 12/1970 |
| FR | 77 29075 | 9/1977 |
| HU | 210122 B | 9/1992 |
| JP | 10321984 | 12/1998 |
| JP | 2000-143486 | 5/2000 |
| WO | 9515750 | 12/1993 |
| WO | 9738685 | 4/1996 |
| WO | 9819690 | 11/1996 |
| WO | 9706795 | 2/1997 |
| WO | WO 97/38686 | 10/1997 |
| WO | WO 98/56497 | 12/1998 |
| WO | WO 99/45913 | 9/1999 |
| WO | 0025764 | 5/2000 |
| WO | 0051596 | 9/2000 |
| WO | WO 01/56609 | 8/2001 |
| WO | WO 02/00213 | 1/2002 |
| WO | WO 02/47493 | 6/2002 |
| WO | WO 02/062322 | 8/2002 |
| WO | WO 02/066002 | 8/2002 |
| WO | WO 2004/032916 | 4/2004 |
| WO | WO 2004/049095 | 6/2004 |

OTHER PUBLICATIONS

Savi et al.; Article from Entrez-PubMed web page entitled: SR 121787, a new orally active fibrinogen receptor antagonist; Sep, 80(3):469-76.

Banno et al.; Article from Entrez-PubMed web page entitled: Antiaggregatory, antithrombotic effects of MS-180, a novel platelet glycoprotein IIb/IIIa receptor antagonist; Eur J Pharmacol Feb. 19, 1999; 367 (2-3): 275-82.

Ramjit et al.; Article from Entrez-PubMed web page entitled: Antithrombotic effects of MK-0852, a platelet fibrinogent receptor antagonist, in canine models of thrombosis; J Pharmacol Exp Ther Sep. 1993; 266(3): 1501-11.

Savi et al.; Article from Entrez-PubMed7.htm web page entitled: SR121787, a new orally active fibrinogen receptor antagonist.; Thromb Haemost Sep. 1998; 80(3): 469-76.

Hoffmann et al.; Article from Entrez-PubMed web page entitled: SR 121787, Prevention of thrombosis and enhancement of thrombolysis in rabbits by SR 121787, a glycoprotein II/III antagonist; J Pharmacol Exp Ther Aug. 1998; 286(2): 670-5.

Packham; Article from Entrez-PubMed web page entitled: Role of platelets in thrombosis and hemostasis; Can J Physiol Pharmacol Mar. 1994; 72(3): 278-84.

Lynch et al.; Article from Entrez-PubMed web page entitled: Nonpeptide glycoprotein IIb/IIIa inhibitors. 5. Antithrombotic effects of MK-0383; J Pharmacol Exp Ther Jan. 1995; 272(1): 20-32.

Kathda et. al.; Articl from Entrez-PubMed web page entitled: The in vitro and in vivo pharmacological profiles of a platelet glycoprotein IIb/IIIa antagonist, NSL-9403, (1997).

Article from Entrez-PubMed web page entitled: antiplatelet and antithrombotic effects of orbofiban, a new orally active GPIIb/IIIa antagonist, in guinea pigs, Ogawa et al. (Mar. 2002).

(Continued)

Primary Examiner—Sreeni Padmanabhan
Assistant Examiner—Timothy E Betton
(74) Attorney, Agent, or Firm—Hovey Williams LLP

(57) ABSTRACT

The present invention provides pharmaceutical uses of betaines, and especially glycine betaine, such as for the treatment of thromboses not induced by hyperhomocystenemia or homocystinuria, of blood disorders, such as blood coagulation and thrombi formation.

15 Claims, No Drawings

OTHER PUBLICATIONS

XP-002123170; Database Chemabs 'Online!; Chemical Abstracts Service, Columbus, OH; Zapadnyuk, B.I. et al.: "Bile-secretory effect of trimethylglycine in normal and atherosclerotic animals of different ages" retrieved from STN Databas accession No. 107:190742 HCA; abstract & Byull. Eksp. Biol. Med. (1987), 104(7), 30-2.

XP002123171; Database Chembas 'Online!; Chemical ABstracts Service, Columbus, OH: Panteleimonova, T.N. et al.: "Effect of trimethylglycine on lipid metabolism in rabbits with experimental atherosclerosis" retrieved from STN; Database accession No. 99:99080 HCA; abstract & Farmakol. Toksikol. (Moscow) (1983), 46(4), 83-5.

XP-000853747; Fazio B Et al: "Treatment of human atherosclerosis with betaine." Minerva Med, (Apr. 25, 1961) 52 1511-6., the whole document.

XP-002123167; P.H. List et al.: "Hagers Handbuch Der Pharmazeutischen Praxis" 1972, Springer-Verlag, Berlin Heidelberg, New York, p. 431.

XP000853853; "Betaine for homocystinuria." Medical Letter on Drugs and Therapeutics, (1997); 39/993 (12)., the whole document.

XP000853897; Wilcken D E et al: "The natural history of vascular disease in homocystinuria and the effects of treatment." Journal of Inherited Metabolic Disease, (Jun. 1997) 20 (2) 295-300., the whole document.

XP-002123168; J.E.F. Reynolds: "Martindale, The Extra Pharmacopoeia";1996, Royal Pharmaceutical Society, London;"Betaine hydrochloride"; p. 1679.

XP002123169; "the merck index"; 1996, Merck & Co, Whithouse Stations, NJ; "Betaine"; p. 198.

Mar at al.; Betaine in wine: answer to the French paradox?; Med Hypothese Nov. 1999; 53(5):383-5.

Salamone et al.; Changes in blood coagulation in experimental subacute poisoning with p-dichlorobenzene. The influence of some lipotropic factors; Journal; Answer 13 of 13; Copyright 2003.

XP001080754; Vinson et al.; New Dug Approvals of 1996—Part 3; University of Mississippi School of Pharmacy; Drug Topics; Mar. 17, 1997; pp. 72-81.

XP-002202249;Napreben;Pharmaprojects; Applied Pharma Research; Company communication, APR, Sep. 1995; whole document.

Matthews et al.; An indirect response model for homecysteine suppression by betaine: optimising the dosage regimen of betaine in homocystinuria; copyright 2002 Blackwell Science Ltd. Br J Clin Pharmacol, 54, 140-146.

Schwahn et al.; Pharmacokinetics of oral betaine in healthy subjects and patients with homocystinuria; copyright 2003 Blackwell Science Ltd. Br J Clin Pharmacol, 55, 6-13.

Bandfield et al.; Naproxen, Naproxen Sodium, and Naproxen Betainate Sodium Monohydrate Salts; Pharmaceutics I; Apr. 14, 2001; 5 pages.

van Hecken et al.; Effect of clopidogrel on naproxen-induced gastrointestinal blood loss in healthy volunteers; Drug Metabol Drug Interact 1998; 14 (3): 193-205.

Rogers J.S., "Hypercoagulable states," W V Med J., Feb. 1993;89(2):61-3, http://www.ncbi.nlm.nih.gov/sites/entrez?Db=pubmed&Cmd=ShowDetailView&TermTo....

Nielsen H.K., "Pathophysiology of venous thromboembolism," Semin Thromb Hemost, 1991;17 Suppl 3:250-3, http://www.ncbi.nlm.nih.gov/sites/entrez?Db=pubmed&Cmd=ShowDetailView&TermTo....

Silver et al., "The caput medusae of hypercoagulability," J. Vasc. Surg., Feb. 2000;31(2):396-405, http://www.ncbi.nom.nih.gov/sites/entrez.

Carman and Fernandez, "A Primary Care Approach to the Patient with Claudication," American Family Physician, vol. 61, No. 4, Feb. 15, 2000, http://www.aafp.org/afp/20000215/1027.html, 8 pages.

Beaufour and Beaufour, "Nouvelles associations antinévralgiques à tolérance améliorée," Brevet Spécial De Médicament, P.V. No. 927.734, No. 2.590, 1964, pp. 1-5.

Feb. 23, 1996 Chinese document (pp. 91-93) with English translation entitled "Homocysteine and Vascular Disease," 5 pages.

Da Silva and Sobel, "Anicoagulants: to bleed or not to bleed, that is the question," Semin Vasc. Surg. Dec. 2002;15(4):256-67, http://www.ncbi.nlm.nih.gov/sites/entrez?Db=pubmed&Cmd=ShowDetailView&TermTo....

JACC Abstracts, Myocardial Ischemia and Infarction, Feb. 2000, 1196-107, pp. 408-409.

Lasch H.G., "Principles of Drug Prevention of Thrombosis," Langenbecks Arch Chir., 1986;369:451-7, http://www.ncbi.nlm.nih.gov/sites/entrez?Db=pubmed&Cmd=ShowDetailView&TermTo....

Marcel et al., From Virchow to red cells (the unended quest)., Ric Clin Lab., 1983;13 Suppl 3:71-81, http://www.ncbi.nlm.nih.gov/sites/entrez?Db=pubmed&Cmd=ShowDetailView&TermTo....

I. Zöllel et al., Betaine-Palmitate Reduces Acetylsalicyclic Acid-induced Gastric Damage in Rats, Scand J. Gastroenterol 2001 (8), pp. 811-816.

Antithrombotic effect of Betaine, Bio Ethic, Jan. 2003, pp. 1-30.

Office Action in U.S. Appl. No. 09/945,391 dated Nov. 5, 2002, 5 pages.

Office Action in U.S. Appl. No. 09/945,391 dated Jun. 4, 2003, 14 pages.

EC-Naprosyn, Naprosyn, Anaprox, Naprosyn, Rx Only, Roche Pharmaceuticals, Copyright 1999-2004 by Roche Laboratories Inc.

Environmental and Health Assessment of Substances in Household Detergents and Cosmetic Detergent Products, Environment Project, 615, 2001, 6.1 Betaines, http:www2.mst.dk/common/Udgivramme/Frame.asp?pg=http://www2.mst.dk/udgiv/Publications/2001/87-7944-596- 9/html/helepubl_eng.htm.

NIAID Home/Anti-HIV/OI Chemical Compound Search/Anti-HIV/OI Chemical Compound Results, http:chemdb.niaid.nih.gov/struct_search/all/url_search.asp?aids_no=008188.

Wyrick P.B. et al., The Microbicidal Agent C31G Inhibits Chlamydia Trachomatis Infectivity in vitro., *Antimicrob Agents Chemother*, Jun. 1997, 41(6): 1335-44, PMID: 9174195.

Thompson, K.A. et al., Assessment of the Anti-Microbial Agent C31G as a Spermicide: Comparison with Nonoxynol-9, *Contraception*, May 1996, 53(5): 313-8, PMID: 8724622.

Chambers, S. et al., The Osmoprotective Properties of Urine for Bacteria: The Protective Effect of Betaine and Human Urine Against Low pH and High Concentrations of Electrolytes, Sugars, and Urea, *J. Infect Dis.*, Dec. 1985, 152(6): 1308-16, PMID: 3905988.

Smith, L.T., Role of Osmolytes in Adaptation of Osmotically Stressed and Chill-Stressed Listeria Monocytogenes Grown in Liquid Media and on Processed Meat Surfaces, *Appl Environ Microbiol*, Sep. 1996, 62(9): 3088-93, PMID: 8795194.

Peddie B.A. et al., Is the Ability of Urinary Tracy Pathogens to Accumulate Glycine Betaine a Factor in the Virulence of Pathogenic Strains?, *J. Lab. Clin. Med.*, Oct. 1996, 128(4): 417-22, PMID: 8833891.

Koskinen, E. et al., A Preliminary Study on the Use of Betaine as a Cryoprotective Agent in Deep Freezing of Stallion Semen, *Zentralbl Veterinarmed A.*, Feb. 1989, 36(2): 110-4, PMID: 2501949.

Swan M.A., Improved Preservation of Ultrastuctural Morphology in Human Spermatozoa Using Betaine in the Primary Fixative, Int. J. Androl., Feb. 1997 20(1): 45-54, PMID: 9202990.

Swan M.A., Improved Preservation of the Ram Spermatozoan Plasma Membrane using Betaine in the Primary Fixative, *J. Microsc*, Sep. 1997, 187(pt 3): 167-9, PMID: 9351233.

Thomas K.C. et al., Effects of Particulate Materials and Osmoprotectants on Very-High-Gravity Ethanolic Fermentation by *Saccharomyces cerevisiae*, Appl Environ Microbiol, May 1994, 60(5): 1519-24, PMID: 8017934.

McGregor et al, "A Controlled Trial of the Effect of Folate Supplements on Homocysteine, Lipids and Hemorheology in End-State Renal Disease," Nephron, vol. 85, No. 3, 2000, 215-220.

Gurfinkel et al., "Fast platelet suppression by lysine acetylsalicylate in chronic stable coronary patients. Potential clinical impact over regular aspirin for coronary syndromes," Clin. Cardiol., Sep. 2000;23(9):697-700.

Klasing et al., "Dietary Betaine Increases Intraepithelial Lymphocytes in the Duodenum of Coccidia-Infected Chicks and Increases Functional Properties of Phagocytes," 2002, *The American Society for Nutritional Sciences*, J. Nutr, 132:2274-2282, 2002.

Schmidt et al., "Total nitric oxide production is low in patients with chronic renal disease," Kidney International, 2000, 58, 1261-1266.

Letter Regarding Dietary Supplement Health Claim for Folic Acid, Vitamin B6, and Vitamin B12 and Vascular Disease, to Jonathan W. Emord of Emord & Associates, PC, from Christine J. Lewis of the FDA, Nov. 28, 2000.

Malinow, "Plasma homocyst(e)ine and arterial occlusive diseases: a mini-review," *Clin. Chem.*, Jan. 1995;41(1):173-6.

al Awami et al., "Homocysteine levels in patients with Raynaud's phenomenon," Vasa. May 2002; 31(2): 87-90.

Stammler et al., "The prevalence of hyperhomocysteinemia in thromboangitis obliterans. Does homocysteine play a role pathogenetically?" *Dtsch Med Wochenschr*, Nov. 15, 1996;121(46):1417-23.

McCarty, "Co-administration of equimolar doses of betaine may alleviate the hepatotoxic risk associated with niacin therapy," Med-Hypothesis, Sep. 2000; 55(3): 189-94.

Letter regarding Petition for Health Claim: Folic Acid, Vitamin B6, and Vitamin B12 Dietary Supplements and Vascular Disease, to Jonathan W. Emord of Emord & Associatees from Christine J. Lewis of the FDA, Feb. 9, 2001.

Birnie et al., "Antimicrobial Evaluation of N-Alkyl Betaines and N-Alkly-N,N-Dimethylamine Oxides with Variations in Chain Length," Antimicrobial Agents and Chemotherapy, Sep. 2000, p. 2514-2517.

English Translation of French Patent 2,590M issued on Jun. 15, 1964, 11 pages.

Korzh, "Relationship Between Endothelial Nitric Oxide Synthesis and Low-Grade Chronic Inflammation," European Atherosclerosis Society, 73rd EAS Congress, Salzburg, Austria, Jul. 7-10, 2002.

Didier et al., "Distal cutaneous necrosis, an unusual etiology: hyperhomocysteinemia," *Ann Dermatol Venereol*, Nov. 1999;126(11):822-5; PMID: 10612875.

Gurfinkel et al., "Fast Platelet Suppression by Lycine Acetylsalicylate in Chronic Stable Coronary Patients. Potential Clinical Impact Over Regular Aspirin for Coronary Syndromes," Abstracts—Myocardiol Ischemia and Infarction, JACC, Feb. 2000, 408A-409A.

* cited by examiner

GLYCINE BETAINE AND ITS USE

RELATED APPLICATIONS

This application is a continuation-in-part of PCT application no. PCT/BE01/00222, filed Dec. 21, 2001, claiming priority from U.S. Ser. No. 09/945,391, filed Aug. 31, 2001 and Belgian application no. 2001/0085, filed Feb. 5, 2001, the contents and teaching and contents of which are hereby incorporated by reference.

FIELD OF THE INVENTION

This invention relates to the use of glycine betaine to eliminate physiopathological vascular attacks. The invention relates to the curative and preventive activity of glycine betaine in the pathogenesis of thrombo-embolic and haemostatic diseases of arterial or venous origin.

Glycine betaine exhibits preventive activity while preventing the formation of thrombi and exhibits a curative activity that prevents the proliferation of thrombi while destroying them. The significance of the present invention is based on the fact that the use of glycine betaine does not result in any risk of haemorrhage or allergy in opposition to the molecules and treatments currently used.

DESCRIPTION OF THE PRIOR ART

Vascular thromboses are a response of the organism that is facing attack on a vessel wall and on the content of cells and plasma thereof. Thrombosis is a localised activation of coagulation with the formation of a thrombus.

The interest to which this pathology has been subjected in recent years has enabled several causative factors to be identified:
  the vessel, the vascular wall and the endothelial cells,
  the role of elements which occur in blood
  the coagulation and fibrinolysis systems, and inhibitors thereof.

Several types of thromboses exist which can occur in arteries, in veins, in the micro-circulation of the organs, in the cavities of the heart and at artificial surfaces in contact with blood. Vascular thromboses are a response to the attack on the vessel wall and on its content of cells and plasma. A thrombosis is an organised mass of blood elements (platelets, red corpuscles and white corpuscles), of fibrin and of other plasma proteins, which are deposited at the surface or which obstruct the free passage of the vascular system.

The mechanisms of thrombosis resemble those of haemostatis, but are pathological due to their abnormal intravascular location.

Thromboses and embolisms are the main reasons for clinical complications associated with cardiovascular diseases and atherosclerosis. According to Virchow, at least three types of thrombogenetic factors determine the location, the extent and the regression of a thrombosis:
  haemodynamic and theological factors;
  endothelial lesion;
  activation of the constituents of blood, particularly of platelets, and of coagulation which results in the formation of thrombin.

Thrombo-embolic disease of arterial or venous origin remains one of the main reasons of death in developed countries.

Arterial thrombosis is often due to a rupture of the atherosclerotic plaque, whereas venous thrombosis results from a deficit of a coagulation inhibitor (AT III) or from a deficit of a fibrinolysis activator (S protein and/or C protein) or more frequently from stasis. In fact, both of these result from an interaction between blood and the vascular wall, from the formation of a venous thrombosis and/or from a haemostatic anomaly. Arterial thrombosis is more often secondary to a parietal anomaly and mainly involves blood platelets. It contributes to a wide variety of clinical pictures depending on the arterial layers involved in the interruption of vascularisation. Thrombosis is mainly capable of affecting the cardiac arteries (coronary), and the arteries of the lower, cerebral or digestive organs. Thus arterial disease favours the formation of the thrombus itself, which is responsible for the majority of terminal vascular occlusions. Moreover, participation of haemostatic disorders and of the thrombus formed at other vascular lesions is evident: aggravation of the lesions of the vascular wall, ischemia and problems in the micro-circulation.

Three therapeutic strategies can be distinguished for the prevention of accidents associated with thromboses:

Anticoagulants. These constitute the major element in the treatment of a patient exhibiting a thrombo-embolic disorder. Heparin and derivatives thereof are currently used. However, the use of heparins can give rise to two major complications, namely haemorrhage or thrombopenia.

K antivitamins (KAV). Prescribed for long-term treatment, these cannot be used in an emergency and cannot be prescribed simultaneously with other anti-aggregants, since they potentiate the haemorrahgic effect thereof.

Platelet antiaggregants. Prescribed to prevent arterial thrombosis associated with atherosclerosis. The main inhibitors of platelet functioning that are currently prescribed are: aspirin, ticlopidine, dipyridamole, and certain non-steroid anti-inflammatory agents such as flurbiprofen and prostacyclin. These treatments are really effective, but have undesirable effects on patients subject to allergies or haemorrhage.

Despite their efficacy, all these treatments necessitate special precautions in use, such as the administration of antidotes, overdose problems and unwanted side effects. These treatments make it necessary to monitor patients, due in particular to haemorrhage-related problems that can arise during or after medication, as well as possible incompatibility with other drugs. It was therefore of interest to identify a molecule having a high antithrombotic potential without undesirable effects. Most surprisingly, glycine betaine has been identified as possessing a high therapeutic potential for in the treatment of thromboses.

Glycine betaine, or betaine of formula $(CH_3)_3N^+-(CH_2)-COO^-$, is a molecule known for its osmo-protective properties and for its cosmetic and pharmaceutical uses. Various pharmaceutical uses of betaine are known, particularly the use of betaine for the treatment of homocystinuria, which causes cardiovascular problems (L. & B. Wilken, J. Inher. Metab. Dis. 1997). Thus patients suffering from homocystinuria, which is a genetic anomaly, exhibit premature atherosclerotic and thrombo-embolic disorders (S. H. Mudd et al. The metabolism and molecular bases of inherited disease, 1995), and of cardiovascular diseases (McCully, Atherosclerosis Rev. 11, 1983). Homocystinuria is a hereditary deficiency, the homozygotic form of which is rare. It is estimated that the prevalence of this homozygotic form corresponds to 1 in 200 in the general population.

Homocystinuria is due to elevated levels of homocysteine in the plasma of the affected patient. The administration of betaine enables the concentration of homocysteine in the blood to be reduced.

Publication WO 951 157 50 proposes the use of ingredients comprising betaine in order to prevent vascular disorders in homocystinuric patients.

Publication WO 98/19690 also relates to patients suffering from an elevated homocysteine level in their blood. The use of betaine amongst other ingredients is intended to reduce the level of homocysteine in the blood, it having been established that homocysteine is a positive factor of risk in the occurrence of cardiovascular diseases, as well as in Alzheimer's disease.

Publication EP 0 347 864 describes the use of betaine together with other ingredients in order to combat the increase in sulfhydryl groups, which are due to cysteine and to homocysteine, in human plasma, and thus to inhibit the formation of atherosclerotic plaques. This anti-atherosclerotic effect is known and is extensively documented. These publications relate to the effect of betaine on the metabolism of lipids (Zapadnyuk et al. Biol. Med. 1987), and on that of cholesterol (Panteleimonova et al., Farmakol. Toksikol, Moscow 1983).

Publication WO 97 38685 describes the use of betaine and taurine for the treatment of complications resulting from ischemia in some organs. Ischemia is a localised stoppage of the bloodstream and only represents one of the pathologies due to thrombosis.

Publication EP 0 781 554 comprises examples which describe experiments on enucleated hearts, i.e. on hearts which have been extracted and isolated from the vascular system. The use of betaine for its known osmo-protective and antiradical properties enables the inventors to claim a protective action thereof on the cardiac muscle.

Other forms of betaine have been proposed (WO 97/06795), but have not hitherto equalled the potency and performance of glycine betaine.

None of these publications discloses the potency of glycine betaine with respect to venous and/or arterial thrombosis, nor its anti-aggregant and anticoagulant potency.

WO 0051596 of applicant, the scope of which is incorporated by reference, discloses the use of betaine for the treatment of thrombosis not induced by homocystinuria. In examples, said application discloses the combination of glycine betaine with a contrast agent. Said document does not disclose the pharmaceutical combination of a therapeutic agent (an agent for treating a trouble or for preventing a trouble for a patient, especially a mammal) with glycine betaine, nor the advantages of such a combination. Possible advantages of such a combination are the reduction of haemorrahgic side effects and/or potentializing the therapeutic effect of said active agent. It has to be noted that due to reduction of haemorrahgic side effect, it is possible to treat more efficiently the pathology, as the dosage of the therapeutic agent can be increased if required. Furthermore, for drugs, such as antithrombotic drugs, it was observed that the antithrombotic effect of the drug was even potentialized.

The invention relates thus among others to:

A pharmaceutical combination comprising a therapeutic effective amount of a therapeutically active agent with at least one haemorrahgic side effect, and a therapeutic effective amount of a compound of formula $(CH_3)_3N^+(CH_2)_nCOO^-$ with n being an integer from 1 to 5, preferably glycine betaine or a pharmaceutically acceptable salt thereof, esters thereof, precursors thereof, precursors thereof, precursors thereof, and mixtures thereof for preventing or reducing said haemorrahgic side effect and/or for potentializing the therapeutic effect of said active agent;

Process of treatment of a patient in need for treating or preventing a trouble by administering to said patient an effective amount of a therapeutic active agent with at least possible one side haemorrahgic side effect, in which an effective amount of a compound of formula $(CH_3)_3N^+(CH_2)_nCOO^-$ with n being an integer from 1 to 5, preferably glycine betaine or a pharmaceutically acceptable salt thereof, esters thereof, precursors thereof, precursors thereof, precursors thereof, and mixtures thereof for preventing or reducing said side effect and/or for potentializing the therapeutic effect of said therapeutically active agent;

A controlled release pharmaceutical system suitable for delivering in a controlled manner to the bloodstream of a mammalian a betaine or an effective amount of a compound of formula $(CH_3)_3N^+(CH_2)_nCOO^-$ with n being an integer from 1 to 5, preferably glycine betaine or a pharmaceutically acceptable salt thereof, esters thereof, precursors thereof, and mixtures thereof;

A controlled release pharmaceutical system for releasing an effective therapeutically amount of at least a compound selected from the group consisting of betaines or an effective amount of a compound of formula $(CH_3)_3N^+(CH_2)_nCOO^-$ with n being an integer from 1 to 5, pharmaceutically acceptable salts thereof, esters thereof, precursors thereof, and mixtures thereof, for treating or preventing blood flow disturbances.

SUMMARY OF THE INVENTION

Glycine betaine, as well as betaine compounds of the general formula $(CH_3)_3N^+-(CH_2)_n-COO^-$, with n varying from 1 to 5 (preferably equal to 1) in the context of the present invention can be used for various clinical applications, such as: coronary thromboses and venous thromboses thromboses and re occlusion of the vascular system following a thrombolysis or an angioplasty infarct, angina pectoris, aneurysm, pulmonary embolism, phlebitis cerebral embolism post-traumatic shock, whether or not of surgical origin prevention of accidents of microcirculation in the following cases: hemophilia, chemotherapy, ageing, oral contraception using oestrogens, obesity, tobacco addiction, prosthesis, diabetes.

prevention of the risks associated with the administration of contrasting ionic and non ionic products.

The extracorporal circulation and the haemodialysis procedures. The blood in contact with artificial surfaces of patients subject to an extracorporal circulation has a risk of formation of platelet nails, of thrombi and embolism. These risks can be prevented by administering the compound(s) of the invention before and/or during and/or after these procedures.

Inflammation phenomena. When binding it with integrine of Mac-1 receptor of the leukocytes and by reducin the expression of mitogenes and pro inflammation cytokines. When acting on the Mac-1 receptor, the compounds of the invention reduce the adhesive and migration properties of the leukocytes, reducing thereby the tissue aggression.

Haemostatic glues. By allowing, in function of pathologies, the gel time of the glues, while reducing secondary effects due to their uses.

Stings and bites of venomous animals. Experimental data show that the injection of compounds of the invention to rats to which a venom lethal dose is injected, delays the death thereof. The compounds of the invention are therefore suitable for entering into antidote composition for venom, possibly in combination with other antivenomous compound(s).

Prevention of blood circulation problems due to contact with artificial surfaces, such as biomaterial elements, prosthesis, etc. (cardiac valves, balloons, catheters, hip prosthesis, stents, etc.). When using these elements with betaine, the secondary effects are reduced. Moreover coating these exogenous materials with betaine avoids problems such as reocclusion, rethrombosis and restinosis.

Metastasis Prevention of cancerous cells. This anti tumoral activity is bound to the fact that cancerous cells released from tumours are transported by the micro thrombi inside the vascular system. These cancerous cells are undetectable by the immune system able to destroy them. Moreover, their incorporation in the micro thrombi facilitates their binding to the vascular system or in the organs, and creates then new cancerous colonies. As the formation of thrombi is function to the adhesion of fibrinogen to glycoprotein IIb IIIa site on the activated platelets, an antagonist of fibrinogen adhesion has an antimetastasis activity by permitting the immune system to detect the cancerous cells during their migration, and by removing the vehicle (thrombus) enabling their transport and their binding. The compounds of the invention can be administered alone or with other anticancerous compounds (simultaneous administration or not) so as to improve their efficiency and the process of angiogenesis during malignant melanomas.

Process for detecting and localizing thrombi by binding compounds of the invention to a portion detectable in vivo and/or in vitro.

Process for avoiding thrombo-embolic problems correlated to air trips. In view of its very low toxicity and its blood fluidifying characteristics, the betaine can be administered in the form of patch, sweets, confectioneries, cookies, drinks, meals, candies, etc. so as to prevent thromboembolic events for airplane/flight passengers.

Sweetener for diabetes, the betaine being or not associated with another sweetener. As Betaine is a residue of sugar production, betaine has some sweetening properties which can be used for the preparation of sweetener with anti aggregation properties. Said sweetener, while avoiding circulation problems bound to diabetes, could improve the efficiency of insulins. It has been demonstrated that the activation of vitronectin receptors facilitates the cell migration and provides the necessary signals for the regulation and proliferation of cells, and potentialises the insulin effect (Ruoslahti, Kidney Int., 1997, 51, 1413-1417).

The compounds of the present invention may also be used in a process for individualizing cells in culture in vitro. The antiaggregants properties of betaine were discovered while performing tests on keratinocyte multilayers. The cells were trypsinized so as to permit individual cell observation, however, prolonges exposure to trypsin leads to cell adhesion impairment. Contacting cell layers with compounds of the present invention resulted in the dissociation of the cell layer into individualized cells, even in the absence of trypsin. Accordingly, compounds of the present invention including the betaines could be used as an alternative to trypsin in cell culture operations.

In another aspect of the present invention, the methods and compounds of the invention can be utilized as anti bacterial and anti infectious agents. This is because bacterial diseases and infectious diseases lead to platelet agglutination and adhesion and the compounds of the present invention are effective in such settings.

Use of a compound of the invention (compound of the general formula $(CH_3)_3N^+$—$(CH_2)_n$—$COO^-$, with n being an integer from 1 to 5, preferably equal to 1, or a mixture of such compounds or one or more pharmaceutically acceptable salts, for the preparation of a pharmaceutical composition for the treatment or for the prevention of troubles bound to one or more glycoproteins, especially to the receptor of one or more glycoproteins, preferably to the receptor of glycoprotein IIb IIIa.

Use of a compound of the invention (compound of the general formula $(CH_3)_3N^+$—$(CH_2)_n$—$COO^-$, with n being an integer from 1 to 5, preferably equal to 1, or a mixture of such compounds or one or more pharmaceutically acceptable salts for potentializing the therapeutical effect of a pharmaceutical active agent.

Platelet aggregation is an essential event in the formation of blood clots and thrombi. In normal conditions, following a vascular lesion, blood clots prevent blood losses by closing the opening. However, in some pathological instances, the formation of a blood clot can reduce partly or completely the blood circulation, with the consequence of a cellular necrosis.

For example, the platelet aggregation and thus the thrombosis at the level of the artherosclerosis plaques is an important factor for the genesis of conditions such as angina pectoris, myocardus infarct, and vessel occlusion following a thrombolysis or an angioplasty. Patients suffering a heart attack are treated with thrombolytic agents such as plasmin activators and the streptokinases which dissolve the fibrin from the clots. A major complication of this therapy is the reocclusion of vessels due to platelet aggregation, which can lead to irreversible damages to the heart, the brain or other organs.

Thrombosis starts with the adhesion of platelets at the vascular lesion sites. The platelet adhesion is initiated by the receptor located at the surface of the platelets that bind to proteins of the extracellular cellular matrix of the exposed endothelium, such as fibrinogen, fibronectin, Von Willebrand factor, as well as other adhesive proteins such as vibronectin, collagen and laminin. Therefore, the activation of platelets is a reply to agonists such as epinephrine, ADP, collagen, the arachidonic acid or the thrombin. This activation leads to the activation of the glycoprotein Ib receptor (GP Ib) and/or of the glycoprotein IIb IIIa receptor (GP IIb IIIa) at the surface of the platelets. This receptor(s) (GP Ib and/or GP IIb IIIa) is/are then available for its/their binding to fibrinogen and the platelet aggregation. The adhesion of the receptor (GP IIb IIIa) to other adhesive proteins such as the Von Willebrand factor also leads the attachment of platelets between them and their aggregation. The adhesion of molecules such as fibrinogen or the Von Willebrand factor to the receptor (GP IIb IIIa) leading the platelet aggregation is an essential step in the formation of the thrombus. The receptor (GP IIb IIIa) is thus a privileged target for the new therapy treating thrombosis and thromboembolitic pathologies. Furthermore, the use of antagonists of the glycoprotein IIb IIIa receptor inhibits the platelet aggregation, while respecting the other haemostasis mechanisms, is highly desirable in the new therapies bound to thrombosis. Several molecules having this antagonist property are marketed with usage restrictions due to immunoreactivity problems, toxicity, allergy or hypersensibility reactions for some patients. A subject matter of the present invention is to propose a molecule, especially a well-known and used molecule of vegetal origin, having this antagonist activity for the glycoprotein IIb IIIa receptor, while not having toxic characteristics.

It is also known that the activation of the vitronectin receptor improves the cell migration and provides regulating signals of the cell proliferation and cell differentiation, and activates the effects of insulin (Ruoslahti, Kidney Int., 1997, 51, 1413-1417). The regulation of the vitronectin receptor is associated with pathological conditions, such as vascular restinosis (Clemetson and Clemetson, Cell. Mol. Life Sci., 1998, 54, 502-513), bone excess resorbtion (Rodan and Rodan, J.

Endocrinol., 1997, 154 Suppl, S47-56), and the angiogenesis process during the malignant melanomas (Cheresh, Cancer Metastasis Rev., 1991, 10, 3-10).

Surprisingly, it has now been found that betaines of formula $(CH_3)_3N^+$—$(CH_2)_n$—$COO^-$, with n being an integer from 1 to 5, and their pharmaceutically acceptable salts, have an antagonist activity for one or more glycoprotein(s) receptors, such as the glycoprotein Ib receptor and the glycoprotein IIb IIIa receptor, by inhibiting the platelet aggregation induced by various agonists. This antagonist activity is not restricted to the glycoprotein site IIb IIIa but to all glycoprotein sites implicated in the cell adhesion of various origins, therebetween.

Platelets are activated by some agonists, whereby their forms, as well as their secretions of their granules, can be modified, and whereby the aggregation thereof can be induced and the formation of clots and thrombi can be produced.

Several endogenous agonists, such as ADP (adenosine-5-diphosphate), serotinine, arachidonic acid, epinephrine, adrenaline, thrombin, collagen, ristocetine are known.

Recently a mechanism of action of these agonists has been identified, namely the activation of the glycoproteic site GP IIb IIIa which causes the adhesion of the circulating fibrinogen (Thromb. Res. 1993, 72, 231-245) and therefore the consolidation of platelet groups and the formation of clots. (Drug of the future, 1994, 19 (2), 135-159)

The actually used platelet aggregation inhibitors are acting only on a single agonist. For example, aspirin is active against the arachidonic acid, ticlopidin is active against ADP, hirudin is active against thrombin. The betaines of the general formula of the invention disclosed here before are actives against various agonists, as well as on fibrinogen, fibronectin, Von Willebrand factor and other adhesive proteins such as vitronectin, collagen, and laminin. This is a major improvement for their efficiency, while preserving the haemostasis mechanism so as to avoid haemorrahgic or bleeding events. Due to their activity by oral administration, said compounds are excellent candidates for pathologies with adhesion of cells between them.

In view of its very low toxicity and its efficiency, the best results have been obtained with glycine betaine (compound of the general formula with n=1). None of the publications to which reference is made in the present specification teach the antagonist activity of the betaine with respect to the glycoprotein IIb IIIa receptor, nor its activity with respect to adhesive proteins. This antagonist activity is not only limited to the site of glycoprotein IIb IIIa, but also to all the other glycoproteic sites acting in the adhesion of cells of various origins there between.

In the present specification, pharmaceutically acceptable salts are salts of betaine which can be administered, such as salts of betaine with hydrochloric acid, sulfuric acid, sulfonic acid, organic acids such as acetic acid, citric acid, tartaric acid, formic acid, etc., as well as the monohydrate radical.

Betaines, preferably glycine betaine, is advantageously administered orally, parenterally, sub cutaneously, by suppositories, tablets, capsules, syrup, etc. Administered doses can vary from 0.001 g to 10 g per kg live body, for example from 0.005 g to 5 g, in particular from 0.01 g to 3 g per kg life body.

Examples of administration forms are: tablets, capsules, patches, injectable forms, releasing forms, sublingual administration form, powder (for example for inhalation therapy, buccal inhalation), syrup, and solution (nebulization, for example for inhalation therapy, buccal inhalation). Preferred administration forms include, subcutaneous injectable dosage forms, patches (to be applied on the skin) and entero soluble oral dosage forms, such as gastro insoluble tablets or capsules, etc. provided with an entero soluble coating or matrix or system.

As the pH of an aqueous glycine betaine solution is comprised between about 6 and about 7, an injectable solution (preferably for a subcutaneous injection) can be prepared by mixing solid glycine betaine with water (sterilized and possibly demineralized). The glycine betaine can be in the form of a powder (lyophilized powder) placed in a vial, water is then added to said vial for the preparation of the solution to be injected. If necessary, some acid (such as hydrochloric) can be added to the solution or to the water to be mixed with the powder.

The injectable dosage form can be a pressurized dosage form, such as an air pressurized dosage form. Subcutaneous injectable forms of glycine betaine, such as intravenous injectable forms, are preferred. Glycine betaine injectable forms are, for example, aqueous solutions containing 0.1 to 50% by weight glycine betaine, advantageously from 0.5 to 30%, preferably from 10 to 20%. The injectable form has a pH, for example, comprised between 5 and 8.5, advantageously from 6 to 7.5, preferably from 6 to 6.5. When the injectable form is prepared by mixing glycine betaine (as a solid form or as a powder form), the pH of the solution is about 6-6.5.

When the glycine betaine is administered by injection, the glycine betaine can be present in a solution of a flexible bag (baxter), for example a flexible bag (baxter) for intravenous administration of a saline solution, or a physiological solution, or a blood transfusion baxter. Such an administration method is conventional in the art and is known to provide a controlled release of the Baxter contents.

Thus, the invention also relates to a bag (flexible bag or baxter) for subcutaneous administration (preferably intravenous administration) containing a solution suitable for subcutaneous administration. As a more specific example, the bag or baxter contains blood or a blood derivative or a blood portion and glycine betaine for subcutaneous administration.

As used herein, subcutaneous injection refers to injections that are placed below the skin including intravenous, intramuscular, and intraarterial injections.

Another subject matter of the invention is a pharmaceutical composition (such as a tablet) containing insulin and betaine, a pharmaceutical composition (such as a tablet) containing an antibiotic and betaine, a pharmaceutical composition (such as a tablet) containing an anti cancerous agent and betaine, a pharmaceutical composition (such as a tablet) containing aspirin and betaine, etc.

A subject matter of the invention is thus a pharmaceutical combination comprising an effective amount of betaine (preferably glycine betaine) and an effective amount of another active agent for the prevention or treatment of troubles.

Advantageously, the pharmaceutical combination comprises an effective amount of an active agent for the treatment and/or prevention of a trouble, said active agent having at least one side effect selected among the group consisting of haemorrahgic events, coagulation troubles, thromboses and associations thereof, and an effective amount of a compound of formula $(CH_3)_3N^+$—$(CH_2)_n$—$COO^-$, with n being an integer from 1 to 5, preferably equal to 1, for preventing at least 50%, advantageously at least 75%, preferably at least 90%, most preferably substantially completely said troubles and/or for reducing the seriousness of said side effect, advantageously of a factor of at least 50%, preferably of at least 75%, most preferably of at least 90%, and especially substantially completely. Betaine is preferably used as anti haemorrahgic agent in said combination. Betaine is also preferably used as an antidote to an haemorrahgic agent in said combination.

The pharmaceutical combination can be in the form of a kit, so as to prepare the combination before administration or during the administration.

Side effects are defined as being events observed in more than 2% of the patients in treatment with the active agent. By combining said active agent with betaine, it is possible to reduce drastically said events, for example, to less than 2%, as well as the importance or gravity of said events.

The active agent with possible side effect is advantageously selected among the group consisting of contrast agents, anti inflammatory agents, anti aggregation agents, anti coagulation agents, anti thrombotic agents, thrombolytic agents, Tpa agents, anti cholesterol agents, anti vitamin K, and mixtures thereof. Specific examples of such agents are glycoaminoglycans, heparins (such unfractioned heparin, standard heparin, low molecular heparins, heparinoid, and mixtures thereof), heparin-like molecules (such as heparinoid, danaparoid, orgaran, fragmin, dalteparin, enoxaparine, lovenox, ardeparin, normiflo and mixtures thereof), thrombin inhibitor (such as argatroban, novastan, and mixtures thereof), aspirin, anti inflammatory agents (such as non steroid anti inflammatory agents), anti aggregation agents, anti coagulation agents, antiplatelet agents (such as dextrans, dipryridamole, sulfinpyrazone, ticlodipine, abcximab, tirofiban, mixtures thereof), anti thrombotic agents, thrombolytic agents (such as human recombinant activated protein, tissue plasminogen activator, urokinase, streptokinase, anistreplase/APSAC, and mixtures thereof), anti cholesterol agents, anti vitamin K, Tpa agents (tissue plasminogen activator), glycoaminoglycans, heparinoid agents, hirudins, anti vitamin K, warfarins, coumadin, coumarin, agents of the statin family, ticlopidine, statin agents, cerivastatine, simvastatin, lovastatin, agents of the statin family, cerivastatine (Baycol), simvastatin, lovastatin, etc.

The invention relates also to the use of a compound of formula $(CH_3)_3N^+(CH_2)_nCOO^-$ with n being an integer from 1 to 5, preferably glycine betaine or a pharmaceutically acceptable salt thereof, esters thereof, precursors thereof, and mixtures thereof, as active antidote agent for the preparation of an antidote composition, for example for combating haemorrahgic troubles, such as haemorrahgic troubles caused by one or more agents selected from the group consisting of: contrast agents, anti inflammatory agents, anti aggregation agents, anti coagulation agents, anti thrombotic agents, thrombolytic agents, Tpa agents, anti cholesterol agents, anti vitamin K and mixtures thereof. Specific examples of such agents are glycoaminoglycans, heparins (such unfractioned heparin, standard heparin, low molecular heparin, heparinoid, and mixtures thereof), heparin-like molecules (such as heparinoid, danaparoid, orgaran, fragmin, dalteparin, enoxaparine, lovenox, ardeparin, normiflo and mixtures thereof), thrombin inhibitors (such as argatroban, novastan, and mixtures thereof), aspirin, anti inflammatory agents (such as non steroid anti inflammatory agents), anti aggregation agents, anti coagulation agents, antiplatelet agents (such as dextrans, dipryridamole, sulfinpyrazone, ticlodipine, abcximab, tirofiban, mixtures thereof), anti thrombotic agents, thrombolytic agents (such as human recombinant activated protein, tissue plasminogen activator, urokinase, streptokinase, anistreplase/APSAC, and mixtures thereof), anti cholesterol agents, anti vitamin K, Tpa agents (tissue plasminogen activator), glycoaminoglycans, heparinoid agents, hirudins, anti vitamin K, warfarins, coumadin, coumarin, agents of the statin family, ticlopidine, statin agents, cerivastatine, simvastatin, lovastatin, agents of the statin family, cerivastatine (Baycol), simvastatin, lovastatin, etc.

Examples of antithrombotic and/or non haemorrahgic formulations in the scope of the present invention can be a combination of therapeutically effective amounts of compound(s) of formula $(CH_3)_3N^+(CH_2)_nCOO^-$ with n being an integer from 1 to 5, pharmaceutically acceptable salts thereof, esters thereof, precursors thereof and mixtures thereof, and therapeutically effective amounts of one or more compound(s), pharmaceutically acceptable salts thereof, esters thereof, precursors thereof and mixtures thereof, selected from the group consisting of: anti aggregants such as abciximab, acetylsalicylate basic aluminium, acetylsalicylate carbonate sodium, acetylsalicylate lysine, acetylsalicylic acid, aloxiprine, anagreli chlorydrate, bencyclane furamate, carbasalate calcium, clopidogrel sulfate, epoprostenol sodium, epifibati, hydroxychloroquine sulfate, iloprost, nicergoline, nifepidine, pyricarbate, sulfinpyrazone, ticlopidine chlorhydrate, tirofiban chlorhydrate, verapamil chlorhydrate, and compounds structurally similar to one of the preceding anti aggregant compounds, and/or anticoagulants such as acenocoumarol, anisindione, biscoumacetate ethyl, bromindione, coumetarol, dalteparine sodium, sirudine, xtran sulfate, enoxaparine sodium, fluindione, heparinate magnesium, heparin calcium, heparine sodium, lepirudine nadroparine calcium, oxazidione, pentosane polyester sulfuric, phenindione, phenprocoumone, reviparine sodium, tinzaparine sodium, tioclomarol, warfarine sodium, and compounds structurally similar to one of the preceding anti coagulant compounds, and/or fibrinolytics such as altepase, anistreplase, atorvastatine calcium, bromelaines, ciprofibrate, defibrotide, fluvastatine sodium, glicazide, lovastatine, lys-plasminogene, phenformine, pravastatine sodium, reteplase, simvastatine, streptokinase, urokinase, and compounds structurally similar to one of the preceding fibrinolytic compounds. Of course, mixtures of any of the above are also embraced by the present invention.

These antithrombotic and/or non-haemorrahgic formulations can be preparations for oral, rectal, parenteral, transdermal, extracorporal, intracorporal administration. For example, for said combinations, the weight ratio between [compound(s) of formula $(CH_3)_3N^+(CH_2)_nCOO^-$ with n being an integer from 1 to 5, pharmaceutically acceptable salts thereof, esters thereof, precursors thereof and mixtures thereof]/[anti aggregants agents and/or anticoagulant agents and/or fibrinolytic agents and/or mixture thereof] is comprise between about 50/1 and 1/50, advantageously between 25/1 and 1/2, preferably between 10/1 and 1/1.

In one embodiment of the present invention, betaine due to its antithrombotic properties may be used to ameliorate the antithrombotic effect of the cited above anti aggregants and/or anticoagulant and/or fibrinolytic agents.

The combined pharmaceutical form of antidote can be a combination of anti coagulant antagonists (such as protamine, vitamine K1, mixtures thereof), and/or thrombolytic agent antagonists (amiocaproic acid, tranexamic acid and mixtures thereof) and a compound of formula $(CH_3)_3N^+(CH_2)_nCOO^-$ with n being an integer from 1 to 5, pharmaceutically acceptable salts thereof, esters thereof, precursors thereof and mixtures thereof.

These combined forms of antidote can be preparations for oral, rectal, parenteral, transdermal, extracorporal, intracorporal administration.

The antithrombotic and/or non haemorrahgic formulations as described above can be combined to the combined pharmaceutical form of antidote as described above.

In one embodiment of the present invention, a compound of formula $(CH_3)_3N^+(CH_2)_nCOO^-$ with n being an integer from 1 to 5, pharmaceutically acceptable salts thereof, esters thereof, precursors thereof and mixtures thereof may be used to treat haemophilia due to it's anti haemorrahgic properties.

In one embodiment of the present invention, a compound of formula $(CH_3)_3N^+(CH_2)_nCOO^-$ with n being an integer from 1 to 5 may be used in combination to ameliorate the anti haemophilia drugs potency due to it's anti haemorrahgic properties.

The combined pharmaceutical form can be a form in which the active agent and the betaine are administered simultaneously or successively, using the same administration way or different administration ways. As specific examples, when using different administration ways, the betaine is administered in the form of a patch or by subcutaneous injection, while the other active agent is administered by oral way or by injection (subcutaneous, venous). When the combined pharmaceutical form is administered using the same administration way, the dosage form is advantageously an injectable form (such as a venous injectable form), but is preferably an oral dosage form, most preferably a solid or semi-solid dosage form. When using a dosage form, the active agent is advantageously in the form of pellets or micropellets or particles which are coated with a betaine-containing layer. The coated particles or pellets can be further coated with an enterosoluble coating which is gastric insoluble or placed in a matrix or capsule which is enterosoluble and gastric insoluble. Preferably, at least the glycine betaine is in a form suitable for subcutaneous injection (preferably intra venous injection) or in a form adapted for the preparation of a form suitable for subcutaneous injection (preferably intravenous injection).

The invention further relates to a process of treatment of a patient in need or for preventing troubles for a patient, by administering to said patient a therapeutically effective amount of an therapeutic active agent having at least one side effect selected among the group consisting of haemorrahgic events, coagulation troubles, thromboses and associations thereof, in which before and/or during and/or after said administration (preferably before and/or during) said patient is administered a therapeutically effective amount of a compound of formula $(CH_3)_3N^+$—$(CH_2)_n$—$COO^-$, with n being an integer from 1 to 5, preferably equal to 1, for preventing at least 50%, advantageously at least 75%, preferably at least 90%, most preferably substantially completely said troubles and/or for reducing the seriousness of said side effect, advantageously by a factor of at least 50%, preferably of at least 75%, most preferably of at least 90%, and especially substantially completely. Glycine betaine is preferably subcutaneously injected (most preferably by intravenous injection).

The present invention relates to a controlled release preparation or device of betaine and, to processes for its preparation and to its medical use. In particular, the invention relates to a controlled release preparation comprising betaine, preferably glycine betaine or a pharmaceutically acceptable salt thereof.

Betaine is a compound of formula $(CH_3)_3 N^+(CH_2)_n COO^-$ with n being advantageously an integer of 1 to 5. Conventional preparations in the form of syrup, or powder have been commercially available for many years for use in the treatment of homocystinuria. Such preparations, however, do not provide a controlled release of the betaines. Moreover, despite betaine's long-standing use, controlled release preparations for oral, rectal, parenteral, transdermal, extracorporal, intracorporal administration containing betaine as an active ingredient have not even previously been described, nor suggested in the literature.

It is therefore an object of the present invention to provide an oral, rectal, parenteral, transdermal, extracorporal, or intracorporal controlled release of a betaine, preferably glycine betaine preparation suitable for at least 5 minutes, such as for at least 10 minutes, . . . up to twelve-hourly (e.g. up to twenty-four hourly or even more, such as for a week, two weeks, one month, three months) administration for the treatment of a mammalian.

The present invention therefore provides a controlled release preparation and/or device comprising betaine, preferably glycine betaine or a pharmaceutically acceptable salt thereof or ester thereof for body (oral, rectal, parenteral, transdermal, extracorporal, intracorporal, etc.) administration.

Suitable pharmaceutically acceptable salts of betaine, preferably glycine betaine for use according to the present invention are those conventionally known in the art such as pharmaceutically acceptable acid addition salts. The anhydrous salt is particularly preferred.

The invention relates to a controlled release pharmaceutical system suitable for delivering in a controlled manner to the bloodstream of a mammalian a betaine or an effective amount of a compound of formula $(CH_3)_3N^+(CH_2)_nCOO^-$ with n being an integer from 1 to 5, preferably glycine betaine or a pharmaceutically acceptable salt thereof, esters thereof, precursors thereof, precursors thereof, and mixtures thereof, and/or to a controlled release pharmaceutical system suitable for delivering in a controlled manner to the bloodstream of a mammalian as active ingredient at least a compound selected from the group consisting of betaines or an effective amount of a compound of formula $(CH_3)_3N^+(CH_2)_nCOO^-$ with n being an integer from 1 to 5, pharmaceutically acceptable salts thereof, esters thereof, precursors thereof, precursors thereof, precursors thereof, and mixtures thereof. The system of the invention is an oral controlled release preparation or device and/or a transdermal controlled release preparation and/oral transdermal controlled release device, a parenteral controlled release preparation and/or an extracorporal controlled release device and/or an intracorporal controlled release device or preparation and/or is a rectal controlled release preparation and/or a rectal controlled release device and/or a mucous controlled release preparation or device and/or a pulmonary controlled release preparation or device and/or an ocular controlled release preparation or device.

According to an embodiment, the system combines at least two systems selected from the group consisting of: oral controlled release preparations, oral controlled release device, transdermal controlled release preparations, transdermal controlled release devices, parenteral controlled release preparations, parenteral controlled release devices, extracorporal controlled release preparations, extracorporal controlled release devices, intracorporal controlled release preparations, intracorporal controlled release devices, rectal controlled release preparations, rectal controlled release device, mucous controlled release preparations, mucous controlled release devices, pulmonary controlled release preparations, pulmonary controlled release devices, ocular controlled release preparations and ocular controlled release devices. In the system of the invention, the active ingredient is preferably glycine betaine.

The invention relates also to a controlled release pharmaceutical system for releasing an effective therapeutically amount of at least a compound selected from the group consisting of betaines or an effective amount of a compound of formula $(CH_3)_3N^+(CH_2)_nCOO^-$ with n being an integer from 1 to 5, pharmaceutically acceptable salts thereof, esters thereof, precursors thereof, and mixtures thereof, for treating or preventing blood flow disturbances, and to a controlled release pharmaceutical system for releasing an effective therapeutic amount of at least a compound selected from the group consisting of betaines, pharmaceutically acceptable salts thereof, esters thereof, precursors thereof, and mixtures thereof, for treating or preventing thrombosis and/or thromboembolic disorders.

The system of the invention is advantageously a system controlling at least for 10 minutes, advantageously at least for 15 minutes, preferably at least for 30 minutes, the release of at least a compound selected from the group consisting of betaines or an effective amount of a compound of formula $(CH_3)_3N^+(CH_2)_nCOO^-$ with n being an integer from 1 to 5, pharmaceutically acceptable salts thereof, esters thereof, precursors thereof, precursors thereof, precursors thereof, and mixtures thereof.

Still more preferably, the system controls at least for 60 minutes, advantageously at least for 90 minutes, preferably at least for 120 minutes, the release of at least a compound selected from the group consisting of betaines or an effective amount of a compound of formula $(CH_3)_3N^+(CH_2)_nCOO^-$ with n being an integer from 1 to 5, pharmaceutically acceptable salts thereof, esters thereof, precursors thereof, and mixtures thereof. Most preferably the system controls at least for 180 minutes, advantageously at least for 240 minutes, more preferably at least for 360 minutes, still more preferably at least for 1440 minutes, and even more preferably for at least 2160 minutes (for example for 1 week, for two weeks, for one month, etc), the release of at least a compound selected from the group consisting of betaines or an effective amount of a compound of formula $(CH_3)_3N^+(CH_2)_nCOO^-$ with n being an integer from 1 to 5, pharmaceutically acceptable salts thereof, esters thereof, precursors thereof, and mixtures thereof.

According to a possible embodiment, the system and/or the device of the invention comprises one or more electronic devices or chips controlling one or more releasing systems or devices, such as a micro pump(s), a syringe, a balloon, etc.

The invention further relates to the use of betaine, a compound of formula $(CH_3)_3N^+(CH_2)_nCOO^-$ with n being an integer from 1 to 5, pharmaceutically acceptable salts thereof, esters thereof, precursors thereof, and mixtures thereof, for the preparation of a system of the invention and/or to a method for treating or preventing a blood flow disturbance, in which a betaine or a compound of formula $(CH_3)_3N^+(CH_2)_nCOO^-$ with n being an integer from 1 to 5, pharmaceutically acceptable salts thereof, esters thereof, precursors thereof, precursors thereof, precursors thereof, and mixtures thereof is administered in a controlled manner to the blood stream of a mammalian, and/or to a method for treating or preventing thrombosis and/or thromboembolic disorders, in which a betaine or a compound of formula $(CH_3)_3N^+(CH_2)_nCOO^-$ with n being an integer from 1 to 5, pharmaceutically acceptable salts thereof, esters thereof, precursors thereof, and mixtures thereof, is administered in a controlled manner to the blood stream of a mammal.

An example of an oral controlled release preparation according to the present invention is one that achieves slow release of a drug over an extended period of time, thereby extending the duration of drug action over that achieved by conventional delivery. Preferably such a preparation maintains a drug concentration in the blood within the therapeutic range for 12 hours or more, most preferably for 24 hours or more.

The present inventor has found that in order to allow for controlled release betaine, preferably glycine betaine over at least a twelve hour period following oral administration, the in vitro release rate preferably corresponds to the following % rate of betaine, preferably glycine betaine released:

TABLE 1

| TIME (H) | % RELEASED |
|---|---|
| 1 | 0-50 |
| 2 | 0-75 |
| 4 | 3-95 |
| 8 | 10-100 |
| 12 | 20-100 |
| 16 | 30-100 |
| 24 | 50-100 |
| 36 | >80 |

Another preferred preparation especially suited for twice-a-day dosing has an in vitro release rate corresponding to the following % rate of betaine, preferably glycine betaine released:

TABLE 2

| TIME (H) | % RELEASED |
|---|---|
| 1 | 20-50 |
| 2 | 40-75 |
| 4 | 60-95 |
| 8 | 80-100 |
| 12 | 90-100 |

Yet another preferred preparation particularly suited for once-a-day dosing has an in vitro release rate corresponding to the following % rate of betaine, preferably glycine betaine released:

TABLE 3

| TIME (H) | % RELEASED |
|---|---|
| 1 | 0-50 |
| 2 | 0-75 |
| 4 | 10-95 |
| 8 | 35-100 |
| 12 | 55-100 |
| 16 | 70-100 |
| 24 | >90 |

A still further preferred preparation in accordance with the invention also particularly suited for once-a-day dosing has an in vitro release rate corresponding to the following % rate of betaine, preferably glycine betaine released.

TABLE 4

| TIME (H) | % RELEASED |
|---|---|
| 1 | 0-30 |
| 2 | 0-40 |
| 4 | 3-55 |
| 8 | 10-65 |
| 12 | 20-75 |
| 16 | 30-88 |
| 24 | 50-100 |
| 36 | >80 |

More preferably a preparation for once-a-day dosing has an in vitro release rate substantially as follows;

| TIME (H) | % BETAINE, PREFERABLY GLYCINE BETAINE RELEASED |
|---|---|
| 1 | 15-25 |
| 2 | 25-35 |
| 4 | 30-45 |
| 8 | 40-60 |
| 12 | 55-70 |
| 16 | 60-75 |

Another preferred dissolution rate in vitro upon release of the controlled release preparation for administration twice daily according to the invention, is between 5 and 50% (by weight) betaine, preferably glycine betaine released after 1 hour, between 10 and 75% (by weight) betaine, preferably glycine betaine released after 2 hours, between 20 and 95% (by weight) betaine, preferably glycine betaine released after 4 hours, between 40 and 100% (by weight) betaine, preferably glycine betaine released after 8 hours, more than 50% (by weight) betaine, preferably glycine betaine released after 12 hours, more than 70% (by weight) released after 18 hours and more than 80% (by weight) betaine, preferably glycine betaine, released after 24 hours.

Furthermore, it is preferred in the case of a controlled release preparation for administration twice daily that, after 8 hours following oral administration between 70 and 95% (by weight) betaine, preferably glycine betaine is absorbed in vivo, between 77 and 97% (by weight) betaine, preferably glycine betaine is absorbed after 10 hours and between 80 and 100% (by weight) betaine, preferably glycine betaine is absorbed after 12 hours.

A formulation in accordance with the invention suitable for twice-a-day dosing may have a $t_{max}$ of 1.5 to 8 hours, preferably 2 to 7 hours, and a $W_{50}$ value in the range 7 to 16 hours. A formulation in accordance with the invention suitable for once-a-day dosing may have a $t_{max}$ in the range of 3 to 6 hours, preferably 4 to 5 hours and a $W_{50}$ value in the range of 10 to 36 hours.

The $W_{50}$ parameter defines the width of the plasma profile at 50% Cmax, i.e. the duration over which the plasma concentrations are equal to or greater than 50% of the peak concentration. The parameter is determined by linear interpolation of the observed data and represents the difference in time between the first (or only) upslope crossing and the last (or only) downslope crossing in the plasma profile.

The in vitro release rates mentioned herein can be are, except where otherwise specified, those obtained by measurement using the Ph. Eur. Paddle Method at 100 rpm in 900 ml 0.1N hydrochloric acid at 37° C. and using any suitable method for detecting the betaine or glycine betaine (such as HPLC, UV detection, etc.,).

The in vivo absorption rate is determined from measurement of plasma concentration against time using the deconvolution technique. A conventional release betaine, preferably glycine betaine, drop preparation (Tramal (trade mark), Grunenthal) was used as the weighting-function and the elimination half life of betaine, preferably glycine betaine was taken as 7.8 hours.

The controlled release preparation according to the invention preferably contains an effective amount of betaine, preferably glycine betaine or a pharmaceutically acceptable salt or esters thereof, or precursors thereof, conveniently in the range of from 50 to 8000 mg, especially 100, 200, 300, 400 to 600, 800 to 1000, 1500 to 5000 mg (calculated as betaine, preferably glycine betaine anhydrous) per dosage unit. The controlled release preparation according to the invention may be presented in any conventional fashion, for example, as granules, spheroids, pellets, multiparticulates, capsules, tablets, sachets, controlled release suspensions, or in any other suitable dosage form incorporating such granules, spheroids, pellets or multiparticulates.

The active ingredient in the preparation according to the invention may suitably be incorporated in a matrix. This may be any matrix that affords controlled release betaine, preferably glycine betaine over at least a twelve hour period and preferably that affords in-vitro dissolution rates and in vivo absorption rates of betaine, preferably glycine betaine within the ranges specified above. Preferably the matrix is a controlled release matrix. Alternatively, normal release matrices having a coating that provides for controlled release of the active ingredient may be used.

Suitable materials for inclusion in a controlled release matrix include (a) Hydrophilic or hydrophobic polymers, such as gums, cellulose ethers, acrylic resins and protein-derived materials. Of these polymers, the cellulose ethers, especially alkylcelluloses are preferred. The preparation may conveniently contain between 1% and 80% (by weight) of one or more hydrophilic or hydrophobic polymers. (b) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred. The preparation may conveniently contain up to 60% (by weight) of at least one digestible, long chain hydrocarbon. (c) Polyalkylene glycols. The preparation may suitably contain up to 60% (by weight) of one or more polyalkylene glycols. One particularly suitable controlled release matrix comprises one or more alkylcelluloses and one or more $C_{12}$-$C_{36}$ aliphatic alcohols. The alkylcellulose is preferably $C_1$-$C_6$ alkyl cellulose, especially ethyl cellulose. The controlled release preparation according to the invention preferably contains from 1 to 20% (by weight), especially from 2 to 15% (by weight) of one or more alkylcelluloses. The aliphatic alcohol may conveniently be lauryl alcohol, myristyl alcohol or stearyl alcohol but is preferably cetyl alcohol or more preferably cetostearyl alcohol. The controlled release preparation suitably contains from 5 to 30% (by weight) of aliphatic alcohol, especially from 10 to 25% (by weight) of aliphatic alcohol.

Optionally the controlled release matrix may also contain other pharmaceutically acceptable ingredients which are conventional in the pharmaceutical art such as diluents, lubricants, binders, granulating aids, colorants, flavorants, surfactants, pH adjusters, anti-adherents and gildants, e.g. dibutyl sebacate, ammonium hydroxide, oleic acid and colloidal silica, as well as combinations of any of the above.

The controlled release preparation according to the invention may conveniently be film coated using any film coating material conventional in the pharmaceutical art. Preferably an aqueous film coating is used. Alternatively, the controlled release preparation according to the invention may comprise a normal release matrix having a controlled release coating. Preferably the preparation comprises film-coated spheroids containing the active ingredient and a spheronising agent. The spheronising agent may be any suitable pharmaceutically acceptable material that may be spheronised together with the active ingredient to form spheroids. A preferred spheronising agent is microcrystalline cellulose. The microcrystalline cellulose used may suitably be, for example, Avicel PH 101 or Avicel PH 102 (Trade Marks, FMC Corporation). Optionally the spheroids may contain other pharmaceutically acceptable ingredients conventional in the pharmaceutical art such as binders, bulking agents and colorants. Suitable binders include water soluble polymers, water soluble hydroxyalkyl celluloses such as hydroxypropylcellulose or water insoluble polymers (which may also contribute controlled release properties) such as acrylic polymers or copolymers for example ethylcellulose. Suitable bulking agents include lactose.

The spheroids are coated with a material that permits release of the active ingredient at a controlled rate in an aqueous medium. Suitable controlled release coating materials include water insoluble waxes and polymers such as polymethacrylates (for example Eudragit polymers, Trade Mark) or water insoluble celluloses, particularly ethylcellulose. Optionally, water-soluble polymers such as polyvinylpyrrolidone or water-soluble celluloses such as hydroxypropylmethylcellulose or hydroxypropylcellulose may be included. Optionally other water-soluble agents such as polysorbate 80 may be added.

Alternatively the drug may be coated onto inert non-pareil beads and the drug loaded beads coated with a material that permits control of the release of the active ingredient into the aqueous medium.

In a further aspect, the present invention provides a process for preparing a controlled release preparation according to the present invention comprising incorporating betaine, preferably glycine betaine or a pharmaceutically acceptable salt thereof, in a controlled release matrix. The process generally includes the steps of: (a) granulating a mixture comprising betaine, preferably glycine betaine or a pharmaceutically acceptable salt thereof and one or more alkylcelluloses, (b) mixing the alkylcellulose containing granules with one or more $C_{12-36}$ aliphatic alcohols; and optionally, (c) shaping and compressing the granules, and film coating, if desired; or (d) granulating a mixture comprising betaine, preferably glycine betaine or a pharmaceutically acceptable salt thereof, lactose and one or more alkylcelluloses with one or more $C_{12-36}$ aliphatic alcohol; and, optionally, (e) shaping and compressing the granules, and film coating, if desired.

The controlled release preparation according to the invention may also be prepared in the form of film coated spheroids by granulating the mixture comprising betaine, preferably glycine betaine or a pharmaceutically acceptable salt thereof and a spheronising agent; extruding the granulated mixture to give an extrudate; spheronising the extrudate until spheroids are formed; and coating the spheroids with a film coat.

One preferred form of unit dose form in accordance with the invention comprises a capsule filled with controlled release particles essentially comprising the active ingredient, a hydrophobic fusible carrier or diluent, and optionally a hydrophilic release modifier. In particular, the controlled release particles are preferably prepared by a process which comprises forming a mixture of dry active ingredient and fusible release control materials followed by mechanically working the mixture in a high speed mixer with an energy input sufficient to melt or soften the fusible material whereby it forms particles with the active ingredient. The resultant particles, after cooling, are suitably sieved to give particles having a size range from 0.1 to 3.0 min, preferably 0.25 to 2.0 mm. An example according to the invention is described below which is suitable for the commercial production of dosage units.

When using such a processing technique it has been found that, in order most readily to achieve the desired release characteristics (both in vivo and in vitro as discussed above), the composition to be processed should comprise two essential ingredients namely: betaine, preferably glycine betaine or salt thereof; and hydrophobic fusible carrier or diluent; optionally together with a release control component comprising a water-soluble fusible material or a particulate soluble or insoluble organic or inorganic material.

The inventor found that the total amount of betaine, preferably glycine betaine or pharmaceutically acceptable salt thereof, in the composition may vary within wide limits, for example from 10 to 90% by weight thereof.

The hydrophobic fusible component (b) should be a hydrophobic material such as a natural or synthetic wax or oil, for example hydrogenated vegetable oil, hydrogenated castor oil, microcrystalline wax, Beeswax, Carnauba wax or glyceryl monostearate, and suitably has a melting point of from 35° to 140° C., preferably 45° to 110° C.

The release modifying component (c), when a water-soluble fusible material, is conveniently a polyethylene glycol and, when a particulate material, is conveniently a pharmaceutically acceptable material such as dicalcium phosphate or lactose.

Another preferred process for the manufacture of a formulation in accordance with the invention comprises: (a) mechanically working in a high-speed mixer, a mixture of betaine, preferably glycine betaine or a pharmaceutically acceptable salt in particulate form and a particulate, hydrophobic fusible carrier or diluent having a melting point from 35° to 140° C. and optionally a release control component comprising a water soluble fusible material, or a particulate soluble or insoluble organic or inorganic material at a speed and energy input which allows the carrier or diluent to melt or soften, whereby it forms agglomerates; (b) breaking down the larger agglomerates to give controlled release seeds; and (c) continuing mechanically working with optionally a further addition of low percentage of the carrier or diluent; optionally repeating steps (c) and possibly (b) one or more times. This process is capable of giving a high yield (over 80%) of particles in a desired size range, with a desired uniformity of release rate of betaine, preferably glycine betaine or salt thereof. The resulting particles may be sieved to eliminate any over-or undersized material then formed into the desired dosage units by for example, encapsulation into hard gelatin capsules containing the required dose of the active substance or by compression into tablets. In this method in accordance with the invention preferably all the betaine, preferably glycine betaine or salt thereof is added in step (a) together with a major portion of the hydrophobic fusible release control material used. Preferably the amount of fusible release control material added in step (a) is between 10% and 90% w/w of the total amount of ingredients added in the entire manufacturing operation, more preferably between 20% and 70% w/w.

Stage (a) of the process may be carried out in conventional high-speed mixers with a standard stainless steel interior, e.g. a Collette Vactron 75 or equivalent mixer. The mixture is processed until a bed temperature of about 40° C. or above is achieved and the resulting mixture acquires a cohesive granular texture, with particle sizes ranging from about 1-3 mm to fine powder in the case of non-aggregated original material. Such material, in the case of the embodiments described below, has the appearance of agglomerates which, upon cooling below 40° C. have structural integrity and resistance to crushing between the fingers. At this stage the agglomerates are of an irregular size, shape and appearance. The agglomerates are preferably allowed to cool. The temperature to which it cools is not critical and a temperature in the range room temperature to 37° C. may be conveniently used.

The agglomerates are broken down by any suitable means, which will comminute oversize agglomerates and produce a mixture of powder and small particles preferably with a diameter under 2 mm. It is currently preferred to carry out the classification using a Jackson Crockatt granulator using a suitable sized mesh, or a Comil with an appropriate sized screen. It was found that if too small a mesh size is used in the aforementioned apparatus, the agglomerates melting under the action of the beater or impeller will clog the mesh and prevent further throughput of mixture, thus reducing yield. A mesh size of 12 has been found adequate. The classified material is returned to the high speed mixer and processing continued. It is believed that this leads to cementation of the finer particles into particles of uniform size range.

In one preferred form of the method of the invention, processing of the classified materials is continued, until the hydrophobic fusible materials used begin to soften/melt and optionally, additional hydrophobic fusible material is then added. Mixing is continued until the mixture has been transformed into particles of the desired predetermined size range. In order to ensure uniform energy input into the ingredients in the high speed mixer, it is preferred to supply at least part of the energy by means of microwave energy. Energy may also be delivered through other means such as by a heating jacket or via the mixer impeller and chopper blades.

After the particles have been formed, they are cooled or allowed to cool, and may then be sieved to remove any over or undersized material. The resulting particles may be used to prepare dosage units in accordance with the invention in the form of e.g. tablets or capsules in manners known per se.

The inventor has also found that particles containing betaine, preferably glycine betaine or a salt thereof produced by a melt processing as described in application PCT/SE93/00225 and the process described and claimed in our prior unpublished UK application No. 9324045.5 filed on Nov. 23, 1993 as well as the process described herein are particularly useful for processing into the form of tablets.

The inventor found that by suitable selection of the materials used in forming the particles and in the tabletting and the proportions in which they are used, enables a significant degree of control in the ultimate dissolution and release rates of the betaine, preferably glycine betaine or salt thereof from the compressed tablets.

Usually, to form a tablet in accordance with the invention, particles prepared as described above will be admixed with tabletting excipients e.g. one or more or the standard excipients such as diluents, lubricants, binding agents, flow aids, disintegrating agents, surface active agents or water soluble polymeric materials. Suitable diluents are e.g. microcrystalline cellulose, lactose and dicalcium phosphate. Suitable lubricants are e.g. magnesium stearate and sodium stearyl fumarate. Suitable binding agents are e.g. hydroxypropyl methyl cellulose, polyvidone and methyl cellulose. Suitable disintegrating agents are starch, sodium starch glycolate, crospovidone and croscarmalose sodium. Suitable surface active are Poloxamer 188.RTM, polysorbate 80, and sodium lauryl sulfate. Suitable flow aids are talc colloidal anhydrous silica. Suitable water-soluble polymers are PEG with molecular weights in the range 1000 to 6000.

To produce tablets in accordance with the invention, particles produced in accordance with the invention may be mixed or blended with the desired excipient(s), if any, using conventional procedures, e.g. using a Y-Cone or bin-blender, and the resulting mixture compressed according to conventional tabletting procedure using a suitable size tabletting mold. Tablets can be produced using conventional tabletting machines, and in the embodiments described below were produced on standard single punch F3 Manesty machine or Kilian RLE15 rotary tablet machine.

Generally speaking, it has been found that even with such a highly water-soluble active agent as betaine, preferably glycine betaine or salt thereof tablets formed by compression according to standard methods, gives very low release rates of the active ingredient e.g. corresponding to release over a period of greater than 24 hours, and preferably more than 36 hours. The inventor found that the release profile can be adjusted in a number of ways. For instance, a higher loading of the drug will be associated with increased release rates; the use of larger proportions of the water soluble fusible material in the particles or surface active agent in the tabletting formulation will also be associated with a higher release rate of the active ingredient. By controlling the relative amounts of these ingredients it is possible to adjust the release profile of the betaine, preferably glycine betaine or salt thereof.

Applicants expressly incorporate the teachings and content of every reference noted herein.

DETAILED DESCRIPTION

The following examples and description illustrate various aspects and preferred embodiments of the present invention. They are not to be construed to limit the claims in any manner whatsoever.

In view of the specification herein, the invention relates to:

The use of a compound of formula $(CH_3)_3N^+-(CH_2)_n-COO^-$ with n being an integer from 1 to 5, preferably equal to 1, or a mixture of such compounds or one or more pharmaceutically acceptable salts thereof for the preparation of a pharmaceutical composition for the treatment or the prevention of troubles bound to one or more glycoproteins, especially to receptors of one or more glycoproteins, preferably to receptor of glycoprotein IIb IIIa.

The use of a compound of formula $(CH_3)_3N^+-(CH_2)_n-COO^-$ with n being an integer from 1 to 5, preferably equal to 1, or a mixture of such compounds or one or more pharmaceutically acceptable salts thereof for the preparation of a pharmaceutical composition for the treatment or the prevention of troubles bound to one or more glycoproteins, especially to receptors of one or more glycoproteins, preferably to a receptor of glycoprotein IIb IIIa for inhibiting the platelet aggregation.

The use of a compound of formula $(CH_3)_3N^+-(CH_2)_n-COO^-$ with n being an integer from 1 to 5, preferably equal to 1, or a mixture of such compounds or one or more pharmaceutically acceptable salts thereof for the preparation of a pharmaceutical composition for the treatment or the prevention of troubles bound to one or more glycoproteins, especially to receptor of one or more glycoproteins, preferably to receptor of glycoprotein IIb IIIa for avoiding the adhesion of cells there between.

A pharmaceutical composition comprising insulin and at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A pharmaceutical composition comprising an anticancerous agent and at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A pharmaceutical composition comprising an antibiotic and at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as glycoproteic antagonist agent, in particular as an antagonist of the glycoprotein IIb IIIa, for the preparation of a pharmaceutical composition.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to cancer, in particular to the metastasis of cancerous cells.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to blood circulation, in particular to the blood microcirculation.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to nicotine addiction.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to obesity.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutically active agent for the preparation of a pharmaceutical composition for the treatment or the prevention or the stabilization of troubles bound to haemophilia.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to chemotherapy.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of diabetic troubles.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to aging.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to oestrogen oral contraception.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutically active agent for the preparation of a pharmaceutical composition for the treatment or the prevention or the stabilization of troubles bound to extracorporal blood circulation, in particular to troubles bound to dialysis and to haemodialysis.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to inflammation, in particular internal inflammation troubles.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to bites, in particular to bites of venomous animals.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to post traumatic shock or post surgical shock.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to septic shocks.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to haemorrhage, in particular to internal haemorrhage, such as a cerebral haemorrhage.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to embolism, in particular to cerebral embolism and/or pulmonary embolism.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to an infract.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutically active agent for the preparation of a pharmaceutical composition for the treatment or the prevention or the stabilization of troubles bound to aneurysm Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to phlebitis.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to angina pectoris.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of thromboses troubles, in particular troubles bound to reocclusion of the vascular system and/or to thrombolysis and/or to angioplasty.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to the use of haemoplastic or haemostatic glues, in particular fibrinogen glue, fibrin glue, collagen glue, thrombin glue.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to pregnancy.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of thromboses troubles, in particular coronary thrombosis and/or venous thrombosis.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to trips or travel, in particular travel in airplane, buses, trains, racket, space shuttle, preferably travel at speed of more than 200 km/h.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to travel, in particular to travel in pressurized environment.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of bacterial troubles and/or infectious troubles and/or troubles due to virus and/or troubles due to fungus.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of asthmatic troubles.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to osteoporosis.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a therapeutic active agent for the preparation of a pharmaceutical composition for the treatment or the prevention or the stabilization of troubles bound to graft of skin and/or tissue and/or bone and/or cells.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as an antagonist agent for serotinin and/or arachidonic acid and/or epinephrine and/or adrenaline and/or thrombin and/or ristocetine for the preparation of a pharmaceutical composition.

Uses as disclosed herein before for the preparation of a pharmaceutical form, possibly as a kit, containing an active agent different from a compound of formula $(CH_3)_3N^+(CH_2)_nCOO^-$ with n being an integer from 1 to 5, preferably equal to 1, or a mixture of such compounds or one or more pharmaceutically acceptable salts thereof, for the administration (simultaneous or successive, with the same or different administration path) of said other therapeutic active agent and of a compound of formula $(CH_3)_3N^+(CH_2)_nCOO^-$ with n being an integer from 1 to 5, preferably equal to 1, or a mixture of such compounds or one or more pharmaceutically acceptable salts thereof.

A sweetening composition containing at least a sweetener and at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A sweetening composition containing at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as an agent for improving the sweetening property of a sweetener, in particular of a synthetic sweetener.

A process for detecting and/or localising and/or separating thrombi in vitro and/or in vivo, possibly in an extra corporal loop or circuit, in which blood is mixed or added with at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A preserving process for cells and/or platelets in a medium, in particular in a blood medium or a fraction thereof, in which said medium is added or mixed with compound of formula $(CH_3)_3N^+(CH_2)_nCOO^-$ with n being an integer from 1 to 5, preferably equal to 1, or a mixture of such compounds or one or more pharmaceutically acceptable salts thereof.

A process for the isolation and/or individualisation of cells and/or platelets in a medium, in particular in a blood medium or a fraction thereof, in which said medium is added or mixed with at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

Platelet rich plasma (blood plasma) or platelet poor plasma, said plasma containing at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A process for the culture of cells in a medium or on a support or in a bioreactor, in particular in a blood medium or a fraction thereof, in which said medium is added or mixed with at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A process for the preparation of fibrin and/or collagen by reaction of fibrinogen or collagen in presence of at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A glue (such as a haemostatic glue) containing at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A device with a surface in contact with fibrin and/or fibrinogen and/or collagen, said surface being made of and being treated with a composition containing at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A composition containing at least fibrinogen and at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A composition containing at least collagen and at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A process for the treatment of blood or a fraction thereof by osmosis and/or reverse osmosis, in which, before and/or during and/or after the osmosis or reverse osmosis, said blood is added or mixed with at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

A process for the treatment of blood or a fraction thereof by centrifugation, in which, before and/or during and/or after the centrifugation, said blood is added or mixed with at least a compound of formula $(CH_3)_3N^+(CH_2)_nCOO^-$ with n being an integer from 1 to 5, preferably equal to 1, or a mixture of such compounds or one or more pharmaceutically acceptable salts thereof.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof for the preparation of a pharmaceutical or cosmetic composition for the treatment or prevention or stabilization of hair troubles, in particular troubles due to hair losses.

A biological material or synthetic material for implant purposes, especially for bone implant, said material being treated with a compound of formula $(CH_3)_3N^+(CH_2)_nCOO^-$ with n being an integer from 1 to 5, preferably equal to 1, or a mixture of such compounds or one or more pharmaceutically acceptable salts thereof, and/or a composition containing such a compound.

A process of treatment of a patient suffering of a trouble cited hereabove in this specification, in which an effective amount of a compound of formula $(CH_3)_3N^+(CH_2)_nCOO^-$ with n being an integer from 1 to 5, preferably equal to 1, or a mixture of such compounds or one or more pharmaceutically acceptable salts thereof is administered to said patient, so as to treat and/or stabilize said trouble.

A process for preventing a patient to suffer a trouble cited hereabove in this specification, in which an effective amount of a compound of formula $(CH_3)_3N^+(CH_2)_nCOO^-$ with n being an integer from 1 to 5, preferably equal to 1, or a mixture of such compounds or one or more pharmaceutically acceptable salts thereof is administered to said patient, so as to prevent said trouble.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as antiagglutinant agent, for the preparation of a pharmaceutical composition.

Use of a compound of formula $(CH_3)_3N^+(CH_2)_nCOO^-$ with n being an integer from 1 to 5, preferably equal to 1, or a mixture of such compounds or one or more pharmaceutically acceptable salts thereof, as a blood fluidifying agent, for the preparation of a pharmaceutical composition.

EXAMPLES OF THE INVENTION

Apparatus and Methods

Materials

Betaine anhydrous, BETAFIN® (Finnsugar Bioproducts, CULTOR, Helinski)
Rats Wistar, males, weight between 250 and 300 grams
Sodium Thiopental
Aggregometer CHRONOLOG COULTRONIC S.A. France ADP & collagen Laboratoires Stago France Methods The aggregation is made in accordance to the methods of Cardinal & Flower. Pharmacol. Method. 1980, and to American Journal of Clinical Pathology, 1989; 92: 676-679, Sureney. J D. Whole Blood aggregometry. After a keeping period of 8 days, the rats are subjected to a fasting for 12 hours. Betaine is subcutaneously injected one hour before blood sampling. The rats are then anaesthetised with sodium Thiopental administered at a dose of 200 mg/Kg and the blood samples are taken by intracardiac puncture on a trisodium citrate solution (1 volume of solution at 3.8% citrate for 9 volumes of blood).

Activated Coagulation Time (Kaolin)

This test explores the intrinsic coagulation pathway. One hour after sub cutaneous administration of the betaine, 0.8 ml total blood by intracardiac way is injected in a container HR, HaemoTec. These tubes contain the kaolin activator. (Method HaemoTec., automated coagulation timer manufactured by MEDTRONIC HAEMOTEC Inc., Englewood, Colo., USA).

Induced Haemorrahgic Time IHT (E. Dejana. Bleeding time in rats. Thrombosis. Rech. 1982) Blood samples are made before the test. The tail of anaesthetised rat, is dipped for 5 minutes in a water bath at 37° C. so as to provoke a dilatation of the peripheral vessels which are removed and cut at the end, the chronometer being started. The IHT is defined as being the time period comprised between the cutting of end tail and the end of the haemorrhage or bleeding. The end of haemorrhage is defined as the time where the last drop of blood is removed from the tail and no other drop is seen for 180 seconds. The substances were subcutaneously administrated 60 minutes prior to the tail cut.

A/Principle of Laser-induced Thrombosis (Seiffge D. et al., 1989; Weichter W. et al., 1983).

In this model, lesion of the vascular wall is induced by a laser beam. This beam causes a limited lesion of the vascular endothelium (only 1 to 2 cells are destroyed). This laying bare of the sub-endothelium, which is a thrombogenetic surface, results in the adherence of platelets via glycoprotein II. This adherence of platelets is followed by the activation thereof. They form pseudopods and secrete the content of their granules. This activation results in the appearance of glycoproteins IIb-IIIa which are necessary for the aggregation of the platelets between them. This lesion is induced in the mesenteric microcirculation of the rat. It is immediately followed by the formation of a thrombus (in a few seconds). This thrombus, which rapidly enlarges under the influence of the flow of blood, embolises before being formed again.

By this manes, the assessment of the effect of glycine betaine was conducted pharmacologically in conjunction with the study of two active molecules used as a reference; namely acetylsalicylic acid and heparin (of low molecular weight). The assessment also involved the activity of glycine betaine in relation to the prothrombotic effects induced by contrasting products.

B/Stasis-induced Thrombosis

A laparotomy was performed to open the lower vena cava, on which a ligature was placed at $T_0$, followed by subcutaneous injection of glycine betaine at $T_0+2$ hours, followed by withdrawal of the clot and blood samples at $T_0+6$ hours.

C/Experimental Procedure

Male Wistar rats were used for these tests. They weighed between 200 and 250 grams. After an 8-day stabilisation period, the rats were subjected to fasting for 12 hours. They were then anaesthetised, glycine betaine was administered subcutaneously, and the mesentery (laser) or vena cava (stasis) was opened at the end of the experiments.

EXAMPLES

Example 1

This example evaluated the number of emboles and the duration of embolisation after vascular change due to laser firings.

|  | Number of emboles or embolies | Duration of embolisation (minutes) |
| --- | --- | --- |
| Negative control NaCl 0.9% | 5.33 ± 0.58 | 2 ± 0 |
| Glycine betaine 5 mg/kg | 2 ± 0 | 1 ± 0 |
| Acetylsalicylic acid 100 mg/kg | 1 ± 1 | 0.33 ± 0.58 |
| Heparin 2 mg/kg | 2.67 ± 0.52 | 1 ± 0 |

Glycine betaine considerably reduced the number of emboles and the duration of embolisation after vascular change due to laser firings. The results demonstrate its powerful anti-thrombotic activity.

Example 2

This example evaluated the bleeding time caused.
(E. Dejana. Bleeding time in rats. Thrombosis. Rech. 1982)

|  | Bleeding time (seconds) |
| --- | --- |
| Negative control NaCl 0.9% | 101.52 ± 5.7 |
| Glycine betaine 5 mg/kg | 95 ± 5 |
| Acetylsalicylic acid 100 mg/kg | 276.67 ± 20.82 |
| Heparin 2 mg/kg | 313.33 ± 20 |

These results show that glycine betaine maintains the bleeding time that is caused within the values of the negative control. In addition to its anti-thrombotic activity, glycine betaine does not result in any risk of haemorrhage compared with the positive controls.

Example 3

This example evaluated platelet aggregation after vascular change due to laser firings (Cardinal & Flower. Pharmacol. Method. 1980)

|  | Amplitude (ohms) | Velocity (ohms/min) |
| --- | --- | --- |
| Negative control NaCl 0.9% | 13 ± 1 | 9 ± 1 |
| Glycine betaine 5 mg/kg | 0.66 ± 1.15 | 1.66 ± 1.15 |
| Acetylsalicylic acid 100 mg/kg | 2.33 ± 2.08 | 2 ± 1 |
| Heparin 2 mg/kg | 4.33 ± 0.57 | 2.66 ± 0.50 |

These results demonstrate the anti-aggregation effect of glycine betaine.

Example 4

This example evaluated the effect on blood cells.

a/Platelet count

|  | Number of platelets ($10^9$) |
| --- | --- |
| Negative control NaCl 0.9% | 788 ± 30.14 |
| Glycine betaine 5 mg/kg | 804.67 ± 20.03 |
| Acetylsalicylic acid 100 mg/kg | 855.33 ± 63.17 |
| Heparin 2 mg/kg | 777.33 ± 6.43 | b/White corpuscle count

|  | Number of white corpuscles ($10^9$) |
| --- | --- |
| Negative control NaCl 0.9% | 5.03 ± 1 |
| Glycine betaine 5 mg/kg | 4.43 ± 0.32 |
| Acetylsalicylic acid 100 mg/kg | 4.33 ± 1.00 |
| Heparin 2 mg/kg | 5.80 ± 0.10 | c/Red corpuscle count

|  | Number of red corpuscles ($10^{12}$) |
| --- | --- |
| Negative control NaCl 0.9% | 6.56 ± 0.15 |
| Glycine betaine 5 mg/kg | 6.19 ± 0.25 |
| Acetylsalicylic acid 100 mg/kg | 6.15 ± 0.31 |
| Heparin 2 mg/kg | 6.20 ± 0.20 |

The counts of the elements occurring in the blood remained within the values of the negative control and demonstrated the innocuousness of glycine betaine.

Example 5

This example evaluated the Biological Balance.

a/Quick time

|  | QT (seconds) |
| --- | --- |
| Negative control NaCl 0.9% | 17 ± 1 |
| Glycine betaine 5 mg/kg | 16.9 ± 1.05 |
| Acetylsalicylic acid 100 mg/kg | 18.33 ± 2.08 |
| Heparin 2 mg/kg | 29.50 ± 0.52 | b/Activated cephaline time (ACT)

|  | ACT (seconds) |
| --- | --- |
| Negative control NaCl 0.9% | 20.5 ± 0.5 |
| Glycine betaine 5 mg/kg | 39.9 ± 1.05 |
| Acetylsalicylic acid 100 mg/kg | 27.26 ± 1.1 |
| Heparin 2 mg/kg | 39.46 ± 1.36 | c/Fibrinogen analysis

|  | Fibrinogen (g/l) |
| --- | --- |
| Negative control NaCl 0.9% | 2.45 ± 0.19 |
| Glycine betaine 5 mg/kg | 1.7 ± 0.1 |
| Acetylsalicylic acid 100 mg/kg | 2.19 ± 0.33 |
| Heparin 2 mg/kg | 2.13 ± 0.25 | d/Alpha,2-antiplasmin analysis (α2AP)

|  | α2AP (%) |
| --- | --- |
| Negative control NaCl 0.9% | 30.16 ± 0.85 |
| Glycine betaine 5 mg/kg | 29.7 ± 0.68 |
| Acetylsalicylic acid 100 mg/kg | 29.36 ± 0.92 |
| Heparin 2 mg/kg | 29.4 ± 1.01 | e/Antithrombin III analysis (AT III)

|  | AT III (%) |
| --- | --- |
| Negative control NaCl 0.9% | 86 ± 3 |
| Glycine betaine 5 mg/kg | 89.5 ± 1.37 |
| Acetylsalicylic acid 100 mg/kg | 85.33 ± 3.51 |
| Heparin 2 mg/kg | 77.66 ± 1.52 |

Example 6

This example evaluated the activity of glycine betaine as a function of time.

Experimental groups: The product was tested at 5 mg/kg
Laser-induced thrombosis

| Control | NaCl 0.9% |
|---|---|
| Group I | The product was injected 1 hour before the experiment |
| Group II | The product was injected 2 hours before the experiment |
| Group III | The product was injected 3 hours before the experiment |
| Group IV | The product was injected 4 hours before the experiment | a) Effect of the product tested (5 mg/ml/kg) on the bleeding time caused.

| Group | B.T.C. (seconds) |
|---|---|
| NaCl 0.9% | 110 ± 21.2 |
| I | 105 ± 26.2 |
| II | 145 ± 15.52 |
| III | 115.5 ± 14.2 |
| IV | 120 ± 10.13 | b) Effect of the product tested (5 mg/ml/kg) on arterial thrombosis induced by laser beam.

| Group | Number of firings | Number of emboles | Duration of embolisation (minutes) |
|---|---|---|---|
| NaCl 0.9% | 2.5 ± 0.84 | 5.7 ± 1.5 | 2.1 ± 0.69 |
| I | 3.49 ± 1.07 | 1.8 ± 1.44 | 0.51 ± 0.5 |
| II | 3.0 ± 1.5 | 1.4 ± 1.18 | 0.3 ± 0.23 |
| III | 2.50 ± 1.25 | 1.99 ± 0.4 | 1.00 ± 0.5 |
| IV | 2.7 ± 1.0 | 2.2 ± 0.69 | 1.5 ± 0.6 | c) Effect of the product tested (5 mg/kg) on platelet aggregation induced ex vivo.

| Group | Amplitude (Ohms) | Velocity (ohm/minute) |
|---|---|---|
| NaCl 0.9% | 24.23 ± 0.5 | 14.4 ± 2.3 |
| I | 11.33 ± 3.08 | 8.2 ± 0.2 |
| II | 13.2 ± 3.5 | 9.3 ± 1.8 |
| III | 12.7 ± 4.1 | 8.7 ± 1.3 |
| IV | 13 ± 2.8 | 8.7 ± 1.15 | d) Evaluation of the effect of glycine betaine on coagulation factors after repeated administration on 5 days of treatment.

| | ACT (seconds) | Quick time (seconds) | Fibrinogen g/l |
|---|---|---|---|
| Untreated control | 21.25 ± 2.3 | 16.1 ± 1.0 | 3.03 ± 0.45 |
| Glycine betaine (5 mg/kg/day) | 39.3 ± 2.3 | 19.8 ± 1.2 | 2.2 ± 0.1 |

Example 7

This example evaluated the effect of glycine betaine on venous thrombosis induced by stasis.

a) Effect of glycine betaine on clot weight

| | Clot weight (mg) |
|---|---|
| Untreated control | 4.033 ± 2 |
| Glycine betaine (1 mg/kg) | 3.1 ± 0.4 |
| Glycine betaine (2.5 mg/kg) | 1.63 ± 0.76 |
| Glycine betaine (5 mg/kg) | 0.76 ± 0.4 | b) Evaluation of the effect of glycine betaine on plasminogenesis

| | Plasminogenesis % |
|---|---|
| NaCl 0.9% | 2.7 ± 0.33 |
| Glycine betaine (5 mg/kg) | 1.66 ± 0.58 |
| Glycine betaine (2.5 mg/kg) | 2 ± 0.15 |
| Glycine betaine (1 mg/kg) | 2.44 ± 0.58 | c) Evaluation of the effect of glycine betaine on coagulation

| | ACT (seconds) | Quick time (seconds) | Fibrinogen g/l |
|---|---|---|---|
| Untreated control | 30.2 ± 2.7 | 16.1 ± 1.0 | 3.03 ± 0.45 |
| Glycine betaine (1 mg/kg) | 29.1 ± 2.3 | 16.2 ± 1.2 | 2.63 ± 0.3 |
| Glycine betaine (2.5 mg/kg) | 31.2 ± 2.6 | 16.6 ± 0.7 | 2.2 ± 0.17 |
| Glycine betaine (5 mg/kg) | 33.5 ± 1.9 | 15.6 ± 0.4 | 2.32 ± 0.33 | d) Evaluation of the effect of glycine betaine on coagulation factors

| | Anti Xa units/ml | Anti IIa units/ml |
|---|---|---|
| Glycine betaine (5 mg/kg) | 0.35 ± 0.15 | — |
| Glycine betaine (2.5 mg/kg) | 0.14 ± 0.10 | — |
| Glycine betaine (1 mg/kg) | 0.08 ± 0.1 | — |

Treatment with glycine betaine inhibits the thrombo-embolic complications that are initiated by laser firings. In fact, treatment with glycine betaine before laser firings decreases the vascular adherence of platelets and the aggregation thereof.

Treatment with glycine betaine inhibits thrombo-embolic complications. In fact, treatment with glycine betaine before the induction of thrombosis exhibited a high antithrombotic potential with regard to all the parameters that come into play in the process of thrombus formation. Moreover, the results for the biological parameters demonstrate the complete innocuousness of glycine betaine, which, in contrast to the reference products used (aspirin and heparin), does not induce any bleeding effect or undesirable side effect. These features mean that glycine betaine, in addition to its demonstrated efficacy, can be administered to people at risk of haemorrhage as well as to people who would be subject to risk of sensitivity or allergy if given conventional antithrombotic treatments (haemophiliac, allergic). Glycine betaine does not cause thrombopenia or haemorrahgic disorders (Examples 2 & 4). The experimental results of Example 5c show that there is a consumption of fibrinogen.

It should be noted that, under the same experimental conditions for the preservation of blood, glycine betaine appeared to possess a high anti-coagulant capacity compared with tubes containing heparin or EDTA. The effective dose of glycine betaine appeared to be between 3 and 5 mg per haemolysis tube. This experimental result demonstrates the high anticoagulant potential of glycine betaine. It can thus be claimed that glycine betaine can be used as an anticoagulant both for the treatment of the human body in vivo and for the preservation of blood ex vivo.

The activity of glycine betaine was also compared with that of contrasting products. In the context of our research on the anti-thrombotic effects, and in order to complement our preliminary work on the efficacy of glycine betaine, we evaluated the effect of glycine betaine on the increase of the thromboembolic risk associated with the use of contrasting products known for their prothrombotic capacities. The significance of this model is that it enables a direct observation to be made of the formation of a thrombus at the site of the vascular lesion. These results explain the occurrence of thrombotic occlusions during angioplasty, especially amongst patients whose endothelium is already damaged or injured. Coronary angioplasty causes a stripping of the endothelium, exposing collagen, elastin and the smooth muscle cells of the circulating blood, analogously to the experimental thrombosis model employed. Thus, there is a higher incidence of new thrombi amongst patients who have had a recent coronary thrombosis or who have an eccentric coronary plaque.

The administration of contrasting products reduces the number of white corpuscles, the number of red corpuscles, and the number of platelets. Contrasting products interact with leukocytes, induce the liberation of leukotrienes, increase vascular permeability and exert a chemotactic effect. Moreover, contrasting products act to control the expression of P-selectin and cause the adherence of white corpuscles to the vascular endothelium. It has been shown that the use of contrasting products is associated with the occurrence of thrombi in variable amounts depending on the product used.

Two contrasting products were studied Hexabrix® (ionic) (Guerbet SA Corp., Villepinte, France) and ® Iopamidol (non-ionic) Hovione FarmaCiencia SA, Loures, Portugal).

Example 8

This example evaluated the number of emboles and duration of embolisation after vascular changes caused by laser firings and administration of contrasting products.

|  | Number of emboles | Duration of embolisation (minutes) |
| --- | --- | --- |
| Negative control NaCl 0.9% | 5.33 ± 0.58 | 2 ± 0 |
| Hexabrix ® | 8 ± 1 | 3.67 ± 0.58 |

-continued

|  | Number of emboles | Duration of embolisation (minutes) |
| --- | --- | --- |
| Iopamidol ® | 11.67 ± 0.50 | 6.33 ± 0.52 |
| Glycine betaine 5 mg/kg + Hexabrix ® | 4 ± 1 | 2 ± 0 |
| Glycine betaine 5 mg/kg + Iopamidol ® | 5.33 ± 0.58 | 2.33 ± 0.48 |

Example 9

This example evaluated induced bleeding time (IBD)

|  | IBD (seconds) |
| --- | --- |
| Negative control NaCl 0.9% | 101.52 ± 5.7 |
| Hexabrix ® | 195 ± 13.23 |
| Iopamidol ® | 128 ± 7.64 |
| Glycine betaine 5 mg/kg + Hexabrix ® | 150 ± 5 |
| Glycine betaine 5 mg/kg + Iopamidol ® | 111 ± 6.60 |

This example shows a reduction of the induced bleeding time of contrasting agents, and an anti-haemorrahgic effect of the betaine.

Example 10

This example evaluated platelet aggregation after vascular change due to laser firings.

|  | Amplitude (ohm) | Velocity (ohm/min) |
| --- | --- | --- |
| Negative control NaCl 0.9% | 13 ± 1 | 9 ± 1 |
| Hexabrix ® | 6 ± 1 | 5.66 ± 0.57 |
| Iopamidol ® ~ | 15 ± 2.64 | 12.33 ± 0.50 |
| Glycine betaine 5 mg/kg + Hexabrix ® | 2 ± 1 | 5 ± 0 |
| Glycine betaine 5 mg/kg + Iopamidol ® | 4.66 ± 0.52 | 9.33 ± 0.8 |

Example 11

This example evaluated the effect of glycine betaine on blood cells.

a/Platelet count

|  | Number of platelets ($10^9$) |
| --- | --- |
| Negative control NaCl 0.9% | 788.33 ± 30.14 |
| Hexabrix ® | 620 ± 10 |
| Iopamidol ® | 585.67 ± 23.54 |
| Glycine betaine 5 mg/kg + Hexabrix ® | 669.67 ± 7.37 |
| Glycine betaine 5 mg/kg + Iopamidol ® | 704.33 ± 92.33 | b/ White corpuscle count

|  | Number of white corpuscles ($10^{12}$) |
|---|---|
| Negative control NaCl 0.9% | 5.03 ± 0.20 |
| Hexabrix ® | 2.96 ± 0.21 |
| Iopamidol ® | 3.06 ± 0.35 |
| Glycine betaine 5 mg/kg + Hexabrix ® | 4.20 ± 0.1 |
| Glycine betaine 5 mg/kg + Iopamidol ® | 3.9 ± 0.3 | c/ Red corpuscle count

|  | Number of red corpuscles ($10^9$) |
|---|---|
| Negative control NaCl 0.9% | 6.56 ± 0.15 |
| Hexabrix ® | 5.43 ± 0.47 |
| Iopamidol ® | 5.5 ± 0.36 |
| Glycine betaine 5 mg/kg + Hexabrix ® | 6.5 ± 0.15 |
| Glycine betaine 5 mg/kg + Iopamidol ® | 6.6 ± 0.19 |

Example 12

This example evaluated Biological balance.

a/ Quick time

|  | QT (seconds) |
|---|---|
| Negative control NaCl 0.9% | 17 ± 1 |
| Hexabrix ® | 24.13 ± 1 |
| Iopamidol ® | 28.1 ± 0.75 |
| Glycine betaine 5 mg/kg + Hexabrix ® | 16.36 ± 0.56 |
| Glycine betaine 5 mg/kg + Iopamidol ® | 17.83 ± 1.2 | b/ Activated cephaline time (ACT)

|  | ACT (seconds) |
|---|---|
| Negative control NaCl 0.9% | 20.5 ± 0.5 |
| Hexabrix ® | 49.3 ± 1.85 |
| Iopamidol ® | 41.33 ± 0.8 |
| Glycine betaine 5 mg/kg + Hexabrix ® | 25.4 ± 0.61 |
| Glycine betaine 5 mg/kg + Iopamidol ® | 22.4 ± 0.7 | c/ Fibrinogen analysis

|  | Fibrinogen (g/l) |
|---|---|
| Negative control NaCl 0.9% | 2.45 ± 0.19 |
| Hexabrix ® | 1.49 ± 0.18 |
| Iopamidol ® | 1.5 ± 0.8 |
| Glycine betaine 5 mg/kg + Hexabrix ® | 1.7 ± 0.09 |
| Glycine betaine 5 mg/kg + Iopamidol ® | 1.9 ± 0.1 | d/ Alpha,2-antiplasmin analysis (α2AP)

|  | α2AP (%) |
|---|---|
| Negative control NaCl 0.9% | 30.16 ± 0.85 |
| Hexabrix ® | 23.26 ± 1.06 |
| Iopamidol ® | 25.23 ± 0.95 |
| Glycine betaine 5 mg/kg + Hexabrix ® | 25.66 ± 0.09 |
| Glycine betaine 5 mg/kg + Iopamidol ® | 28.13 ± 0.8 | e/ Antithrombin III analysis (AT III)

|  | AT III (%) |
|---|---|
| Negative control NaCl 0.9% | 86.3 ± 3 |
| Hexabrix ® | 81.63 ± 0.66 |
| Iopamidol ® | 70.6 ± 1.51 |
| Glycine betaine 5 mg/kg + Hexabrix ® | 79.1 ± 1.05 |
| Glycine betaine 5 mg/kg + Iopamidol ® | 87.26 ± 0.98 |

Treatment with glycine betaine inhibits the thrombo-embolic complications associated with the use of contrasting products. In fact, treatment with glycine betaine, before or during the injection of contrasting products, reduces the adherence of platelets and their aggregation at vascular level. These results demonstrate the anti-thrombotic and thrombolytic effects of glycine betaine. It should be noted that the contrasting products can have other side effects such as haemostasis in catheters and endothelial lesions due to the administration procedures themselves. Glycine betaine remedies these undesirable effects.

Example 13

This example evaluated aggregation induced with ADP.

Final ADP concentration 5 μM

|  | Amplitude (ohms) | Velocity (ohm/minute) |
|---|---|---|
| Control NaCl 0.9% | 16.4 +/− 1.67 | 13.8 +/− 1.3 |
| Glycine betaine 2.5 mg/kg | 13 +/− 0.82 | 5.75 +/− 0.96 |
| Glycine betaine 5 mg/kg | 7.25 +/− 0.96 | 4.75 +/− 0.5 |
| Glycine betaine 10 mg/kg | 0 +/− 0 | 0 +/− 0 |

The dose effect of the betaine shows its action on the glycoprotein IIb IIIa site, the betaine competing in a dose dependant manner with the agonist (ADP).

Example 14

This example evaluates aggregation induced with collagen. Collagen concentration 10 μgr/ml

|  | Amplitude (ohms) | Velocity (ohm/minute) |
| --- | --- | --- |
| Control NaCl 0.9% | 16.75 +/− 0.96 | 9.75 +/− 0.98 |
| Glycine betaine 2.5 mg/kg | 13.75 +/− 0.96 | 9.25 +/− 2.63 |
| Glycine betaine 5 mg/kg | 5.5 +/− 1.29 | 4.5 +/− 1 |
| Glycine betaine 10 mg/kg | 1.5 +/− 1.29 | 2 +/− 0.82 |

The dose effect of the betaine shows its action on the glycoprotein IIb IIIa site, the betaine competing in a dose dependant manner with the agonist (Collagen).

Example 15

This example evaluated activated coagulation time (subcutaneous administration of betaine at different dosages).

|  | Activated Coagulation time (seconds) | Provoked Haemorrhage time (seconds) |
| --- | --- | --- |
| Control NaCl 0.9% | 48 | 107 |
| Glycine betaine 10 mg/kg | 128 | 105 |
| Glycine betaine 30 mg/kg | 179 | 112 |
| Glycine betaine 50 mg/kg | 215 | 115 |

The activated coagulation time is four times higher at a concentration of 50 mg/kg, while not having an effect on the PHT.

Example 16

This example evaluated Activated Coagulation Time after subcutaneous administration of betaine at 10 mg/kg after 24 hours.

|  | Provoked haemorrhage (seconds) | Activated coagulation time (seconds) |
| --- | --- | --- |
| Control NaCl 0.9% | 105 +/− 5 | 48.4 +/− 8.9 |
| Betaine 10 mg/kg | 114 +/− 12.76 | 71 +/− 3.51 |

Example 17

This example evaluated parameters of Thrombosis induced by laser 24 hours after sub cutaneous administration of betaine at 10 mg/kg.

|  | Number of laser firing | Number of emboles | Embolisation time (minutes) |
| --- | --- | --- | --- |
| Control NaCl 0.9% | 2.33 +/− 0.57 | 5.33 +/− 0.57 | 2 +/− 0 |
| Betaine 10 mg/kg | 3.33 +/− 0.57 | 1 +/− 0 | 0 +/− 0 |

Example 18

This example evaluated Activated Coagulation Time after subcutaneous administration of betaine at 20 mg/kg after 24 hours.

|  | Provoked haemorrhage seconds | Activated coagulation time (seconds) |
| --- | --- | --- |
| Control NaCl 0.9% | 105 +/− 5 | 48.4 +/− 8.9 |
| Betaine 20 mg/kg | 110 +/− 13.22 | 154.66 +/− 11.01 |

Example 19

This example evaluated parameters of Thrombosis induced by laser 24 hours after sub cutaneous administration of betaine at 20 mg/kg.

|  | Number of laser firing | Number of emboles | Embolisation time (minutes) |
| --- | --- | --- | --- |
| Control NaCl 0.9% | 2.33 +/− 0.57 | 5.33 +/− 0.57 | 2 +/− 0 |
| Betaine 10 mg/kg | 3.33 +/− 0.57 | 0.66 +/− 0.57 | 0 +/− 0 |

Example 20

This example evaluated the kinetics of the activated coagulation time after oral administration of betaine at 50 mg/kg.

|  | Induced haemorrhage seconds | Activated coagulation time (seconds) |
| --- | --- | --- |
| Control NaCl 0.9% | 105 +/− 5 | 48.4 +/− 8.9 |
| Betaine 50 mg/kg - 1 hour | 120 +/− 5 | 96 +/− 11.27 |
| Betaine 50 mg/kg - 6 hours | 111 +/− 3.6 | 124.66 +/− 9.29 |
| Betaine 50 mg/kg - 24 hours | 113.33 +/− 18.92 | 64.66 +/− 7.37 |
| Betaine 50 mg/kg - 48 hours | 109 +/− 8.54 | 55.66 +/− 7.02 |

Example 21

This example evaluated the kinetics of parameters of Thrombosis induced by laser and effected at different times for the oral administration of betaine at 50 mg/kg.

|  | Number of laser firing | Number of emboles | Embolisation time (minutes) |
|---|---|---|---|
| Control NaCl 0.9% | 2.33 +/− 0.57 | 5.33 +/− 0.57 | 2 +/− 0 |
| Betaine 50 mg/kg 1 hour | 4 +/− 0 | 0 +/− 0 | 0 +/− 0 |
| Betaine 50 mg/kg 6 hours | 3.66 +/− 0.57 | 2.33 +/− 0.57 | 1 +/− 0 |
| Betaine 50 mg/kg 24 hours | 2.33 +/− 0.57 | 2.33 +/− 0.57 | 1 +/− 0 |
| Betaine 50 mg/kg 48 hours | 2.33 +/− 0.57 | 4.33 +/− 0.57 | 2 +/− 0 |

The dose effect is confirmed in all the studied parameters. The antagonist activity at the glycoprotein IIb IIIa site for the compounds of the invention also applies to other agonists, such as serotinin, arachidonic acid, epinephrine, adrenaline, ristocetine and thrombin.

Example 22

This example describes a human in vivo test. Two volunteers (with a weight of about 70-75 kg), considered as heavy smokers (smoking more than 10 cigarettes/day) have orally taken capsules (gastro soluble) containing 5 g anhydrous glycine betaine/day during 7 days. Before administration of the betaine, the aggregations induced by ADP, by collagen, by epinephrine, by adrenaline, by thrombin, by ristocetine and by arachidonic acid were determined. After one week of treatment, the same platelet aggregations were measured. It appeared from said tests that all the induced platelet aggregations were reduced for all said endogenous agonists of at least 30%. Better results are expected when using oral dosage form with controlled release, such as gastro insoluble, but entero soluble form.

Example 23

This example tested anti-haemorrahgic activity using rats. Some rats received an active agent with haemorrahgic side effect, while other rats received said active agent together with a dose of betaine.

The following products were administered to rats for determining whether glycine betaine has an anti-haemorrahgic effect:

100 mg aspirin per kg life body
100 mg aspirin+50 mg glycine betaine per kg life body
2 mg heparin
2 mg heparin+50 mg glycine betaine
2 mg heparin+10 mg glycine betaine
2 mg heparin+2 mg glycine betaine When inducing a haemorrhage, it was observed that the bleeding time was reduced when glycine betaine was administered. It means therefore that glycine betaine has anti-haemorrahgic properties.

Example 24

Tablets having the following formulation were prepared:
Betaine, preferably glycine betaine Anhydrous: 100 mg/tablet
Lactose Ph. Eur.: 68.0 mg/tablet
Ethylcellulose (Surelease.RTM. 25% solids): 15 mg/tablet
Purified Water Ph. Eur.: 13.3* mg/tablet
Cetostearyl Alcohol Ph. Eur.: 42.00 mg/tablet
(Dehydag wax 0)
Magnesium Stearate Ph. Eur.: 2.00 mg/tablet
Purified Talc Ph. Eur.: 3.00 mg/tablet
*Removed during processing.

Betaine, preferably glycine betaine anhydrous (100 mg) and lactose (68 mg) were granulated, transferred to a fluid bed granulator and sprayed with ethylcellulose (15 mg) and water. The granules were then dried at 60° C. and passed through a 1 mm screen. To the warmed betaine, preferably glycine betaine, containing granules was added molten cetostearyl alcohol (42 mg) and the whole was mixed thoroughly. The granules were allowed to cool and were sieved through a 1.6 mm screen. Purified talc and magnesium stearate were added and mixed with the granules. The granules were then compressed into tablets. The tablets were coated with a film coat having the formulation given below.

Hydropropylmethylcellulose: 0.770 mg/tablet
  Ph. Eur. 15 cps (Methocel E15)
Hydroxypropylmethylcellulose: 3.87 mg/tablet
  (Ph. Eur. 5 cps (Methocel E5)
Opaspray M-1-7111B (33% solids): 2.57 mg/tablet
Polyethylene glycol 400 USNF: 0.520 mg/tablet
Purified Talc Ph. Eur.: 0.270 mg/tablet
Purified Water Ph. Eur.: 55.52* mg/tablet
*Removed during processing.

Example 25

Tablets having the following formulation were prepared:
Betaine, preferably glycine betaine anhydrous: 100.0 mg/tablet
Lactose Ph. Eur.: 58.0 mg/tablet
Ethylcellulose USNF: 15.0 mg/tablet
(Ethocel 45 CP)
Cetostearyl alcohol Ph. Eur.: 52.0 mg/tablet
(Dehydag wax O)
Magnesium stearate Ph. Eur.: 2.00 mg/tablet
Purified talc Ph. Eur.: 3.00 mg/tablet A mixture of betaine, preferably glycine betaine anhydrous (100 mg), lactose (58 mg) and ethylcellulose (15 mg) was granulated while adding molten cetostearyl alcohol (52 mg) and the whole was mixed thoroughly. The granules were allowed to cool and sieved through a 1.6 mm screen. Purified talc and magnesium stearate were added and mixed with the granules. The granules were then compressed into tablets that were coated with a film coat having the formulation given in Example 24.

Example 26

Film coated tablets were produced following the procedure described in Example 25 and having the following formulation:
Betaine, preferably glycine betaine anhydrous: 100.00 mg/tablet
Lactose Ph. Eur.: 70.50 mg/tablet
Hydroxyethylcellulose Ph. Eur.: 12.50 mg/tablet
Cetostearyl alcohol Ph. Eur.: 42.00 mg/tablet Magnesium stearate Ph. Eur.: 2.00 mg/tablet
Purified talc Ph. Eur.: 3.00 mg/tablet In vitro dissolution studies were conducted on tablets prepared as described above. Results are given in Table 5.

TABLE 5

WT % BETAINE, PREFERABLY GLYCINE BETAINE RELEASED

| Time (h) | Example 24 | Example 25 | Example 26 |
|---|---|---|---|
| 1 | 39 | 35 | 43 |
| 2 | 52 | 47 | 60 |
| 4 | 67 | 62 | 84 |
| 8 | 82 | 78 | 97 |
| 12 | 90 | 86 | — |

* Measured on tablet core

Examples 27 and 28

Particles having the formulations given in Table 6 below, were prepared by the steps of: i. Placing the ingredients (a) and (c) (total batch weight 0.7 kg) in the bowl of a 10 liter capacity Collette Gral Mixer (or equivalent) equipped with variable speed mixing and granulating blades; ii. Mixing the ingredients at about 150-1000 rpm whilst applying heat until the contents of the bowl are agglomerated. iii. Classifying the agglomerated material by passage through a Comil and/or Jackson Crockatt to obtain controlled release seeds. iv. Warming and mixing the classified material in the bowl of a 10 liter Collette Gral, until uniform multiparticulates of the desired pre-determined size range are formed in yield of greater than 80%. This takes approximately 5 minutes. v. Discharging the multiparticulates from the mixer and sieving them to separate out the multiparticulates collected between 0.5 and 2 mm aperture sieves.

TABLE 6

| | Example | |
|---|---|---|
| | 27 | 28 |
| (a) Betaine, preferably glycine betaine Anhydrous (Wt %) | 50 | 75 |
| (b) Hydrogenated Vegetable Oil (Wt %) | 50 | 25 |

Example 29

Samples of the particles from Example 4 were blended with magnesium stearate and purified talc using a Y-Cone or bin-blender. The blended mixture was then compressed using either (1) 14×6 mm, (2) 16×7 mm or (3) 18.6×7.5 mm capsule shaped tooling on a single punch F3 Manesty tabletting machine to give tablets giving 200, 300 and 400 mg of betaine, preferably glycine betaine anhydrous. The ingredients per dosage unit amounted to the following:

TABLE 7

| TABLET | MG/TABLET | | |
|---|---|---|---|
| INGREDIENT | 29 (1) | 29 (2) | 29 (3) |
| Betaine, preferably glycine betaine Anhydrous | 200 | 300 | 400 |
| Hydrogenated Vegetable Oil | 200 | 300 | 400 |
| Sub Total | 400 | 600 | 800 |

TABLE 7-continued

| TABLET | MG/TABLET | | |
|---|---|---|---|
| INGREDIENT | 29 (1) | 29 (2) | 29 (3) |
| Purified Talc | 12.63 | 18.95 | 25.26 |
| Magnesium Stearate | 8.42 | 12.63 | 16.84 |

The tablets were assessed by the dissolution using Ph. Eur. Paddle Method 100 rpm, 0.1N HCl.

To assess the non-compressed particles the Ph Eur. Paddle was replaced by a modified Ph Eur. Basket.

The results are shown in Table 8 below:

TABLE 8

| HOURS AFTER | % BETAINE, PREFERABLY GLYCINE BETAINE Anhydrous RELEASED | | | |
|---|---|---|---|---|
| START OF TEST | Particles | Tablet 29 (1) | tablet 29 (2) | Tablet 29 (3) |
| 1 | 54 | 16 | 15 | 15 |
| 2 | 68 | 23 | 20 | 21 |
| 3 | 76 | 28 | 25 | 25 |
| 4 | 82 | 32 | 28 | 28 |
| 6 | 89 | 40 | 35 | 35 |
| 8 | 93 | 46 | 41 | 40 |
| 10 | 96 | 50 | 45 | 45 |
| 12 | 98 | 55 | 49 | 49 |
| 16 | 100 | 63 | 57 | 56 |
| 20 | NR | 70 | 63 | NR |

The first row of results in the table corresponds to betaine in immediate release form and therefore can be used as a control or as a comparitive data set for the controlled release tablets. As shown by the results, the controlled release tablets are effective in reducing the release rate.

Example 30

Samples of the particles from Example 28 were then tabletted using a procedure similar to Example 26 and the ingredients per unit dosage amounted to:

TABLE 9

| TABLET | MG/TABLET | | |
|---|---|---|---|
| INGREDIENT | 30 (4) | 30 (5) | 30 (6) |
| Betaine, preferably glycine betaine Anhydrous | 200 | 300 | 400 |
| Hydrogenated Vegetable Oil | 66.7 | 100 | 133 |
| Sub Total | 266.7 | 400 | 533 |
| Purified Talc | 7.63 | 11.44 | 15.25 |
| Magnesium Stearate | 5.16 | 7.63 | 10.17 |

The tablets and samples of non-compressed multiparticulates (each sample containing 400 mg of betaine, preferably glycine betaine anhydrous) were assessed by the dissolution method also described above. The results are shown in Table 10 below.

TABLE 10

| HOURS AFTER START OF TEST | Particles | Tablet 30 (4) | Tablet 30 (5) | Tablet 30 (6) |
|---|---|---|---|---|
| | % BETAINE, PREFERABLY GLYCINE BETAINE Anhydrous RELEASED | | | |
| 1 | 77 | 43 | 40 | 42 |
| 2 | 92 | 64 | 55 | 56 |

TABLE 10-continued

| HOURS AFTER START OF TEST | Particles | Tablet 30 (4) | Tablet 30 (5) | Tablet 30 (6) |
|---|---|---|---|---|
| | % BETAINE, PREFERABLY GLYCINE BETAINE Anhydrous RELEASED | | | |
| 3 | 98 | 75 | 65 | 66 |
| 4 | 100 | 83 | 72 | 73 |
| 6 | 102 | 94 | 83 | 84 |
| 8 | 102 | 100 | 91 | 91 |
| 10 | 102 | NR | 96 | 97 |

As with the previous results provided in Example 29, the first row of results in this table corresponds to betaine in immediate release form. These results show that by increasing the loading of the highly water soluble betaine, preferably glycine betaine anhydrous (75% w/w in this example compared with 50% w/w in Example 29) a significantly faster release rate of the active ingredient can be achieved.

Example 31

Example 27 was repeated but with the following formulation:

| Betaine, preferably glycine betaine Anhydrous: | 200 mg/tablet |
|---|---|
| Hydrogenated Vegetable Oil: | 163.0 mg/tablet |

The resulting multiparticulates were blended as described in Example 29 with the following:

| Purified Talc | 11.5 mg/tablet |
|---|---|
| Magnesium Stearate | 7.66 mg/tablet |

The blend was then compressed as described in Example 29 but using 15 mm×6.5 mm normal concave capsule shaped plain/plain punches.

The resulting tablets were then assessed by the dissolution method described above. The results are shown in Table 11.

TABLE 11

| HOURS AFTER START OF TEST | % BETAINE, PREFERABLY GLYCINE BETAINE Anhydrous RELEASED |
|---|---|
| 1 | 20 |
| 2 | 27 |
| 3 | 32 |
| 4 | 37 |
| 6 | 44 |
| 8 | 50 |
| 10 | 55 |
| 12 | 60 |
| 16 | 67 |
| 20 | 73 |
| 24 | 77 |

The examples provided above are not meant to be exclusive. Many other variations of the present invention would be obvious to those skilled in the art, and are contemplated to be within the scope of the appended claims.

The man skilled in the art can adjust the release rate of a patch so as to have an adapted betaine concentration in the blood, for a period of for example 6 hours, 12 hours, 24 hours, etc. The patch structure can be as taught in U.S. Pat. Nos. 4,911,916, 4,917,676, 5,536,503 and 5,486,362, the scope of which is incorporated by reference. In said patch structure, a betaine of formula $(CH_3)_3N^+(CH_2)_nCOO^-$ with n being an integer from 1 to 5, preferably glycine betaine or a pharmaceutically acceptable salt thereof, esters thereof, precursors thereof, and mixtures thereof is used as active agent instead of the proposed active agent. The drawings of said patents (especially FIGS. 2 and 3 of U.S. Pat. No. 5,536,503) are incorporated by reference for teaching the possible form and structure of the patch.

Transdermal patches have a variety of advantages including avoidance of the gastrointestinal tract, sustained action that can be readily adjusted, self-administration, and the ability to immediately discontinue dosage. The term transdermal patch is intended to include patches capable of being affixed to the skin of an individual and having a part or component capable of delivering an active agent (such as a betaine of formula $(CH_3)_3N^+(CH_2)_nCOO^-$ with n being an integer from 1 to 5, preferably glycine betaine or a pharmaceutically acceptable salt thereof, esters thereof, precursors thereof, mixtures thereof), in a controlled sustained release manner. Examples of types of patches useful in this invention include those having a diffusion layer matrix and/or multicompartmental type patches. These will be described below for glycine betaine as active agent. There are many transdermal patches known to those of ordinary skill in the art and well described in the prior art. One such patch useful involves a diffusion matrix layer that uses a reticulated macroporous polymeric foam as a framework for holding a viscoelastic glycine betaine-polymer mixture. The patch is for example a multi (4 or more)-layer, laminated composite that is adapted to be adhered to the skin. The outermost layer, backing layer, functions as the primary structural element of the device as well as serving as a protective covering to prevent the glycine betaine from being transmitted from the device via the outermost surface. Backing layer preferably is made of a sheet or film of a resilient elastomer of about 10-75 microns thick. Examples of such elastomers include polyether block amide copolymers, polyethylene methacrylate block copolymers, polyurethanes, silicon elastomers and the like.

The glycine betaine-containing matrix layer functions as a reservoir for glycine betaine (possibly an enhancer), and optionally as a pressure sensitive adhesive. The framework of the matrix is a reticulated macroporous polymeric foam. Preferably the network is essentially completely open pores (90% or greater). The pore rating of the reticulated foam will normally be in the range of about 10-40 pores per linear centimeter and the density (unfilled) will typically be in the range of about 0.01 to 0.5 g/cm3. Suitable polymers from which such foam frameworks may be manufactured include polyurethanes and polyethylenes.

A pressure sensitive adhesive layer covers the exposed face of the matrix layer and a release liner covers the pressure sensitive adhesive. The pressure sensitive adhesive layer is a medical grade adhesive composition having a thickness normally between about 25 and 100 microns. An example of such an adhesive is polydimethylsiloxane (Dow Corning 355 medical grade adhesive).

The pores of the foam are wholly or partly filled with a viscoelastic hydrophobic betaine-permeable polymer (and an enhancer if present). The polymer acts as a carrier for the glycine betaine, while the enhancer acts to control the solubility of the glycine betaine in the polymer and/or absorption of the drug into the skin. The hydrophobic polymer renders the device water-resistant and prevents liquid water from being absorbed by the device, thereby increasing its functionality and wearability. Examples of such polymers are polysiloxanes (silicone polymers), hydrophobic polyacrylates, polyurethanes, plasticized ethylene-vinyl acetate copolymers and the like. An example of a useful enhancer includes Azone™. Another example of a useful dermal permeation enhancer includes transcutol. The mixture including the glycine betaine optionally includes an anti-pruritic agent.

Devices of the foregoing nature are generally described in U.S. Pat. No. 4,911,916, entitled "Diffusion Matrix for Transdermal Drug Administration and Transdermal Drug Delivery Devices Including Same", issued Mar. 27, 1990, the entire disclosure of which is incorporated herein by reference. Such patches may be configured to contain sufficient glycine betaine to release from about five milligrams to 5 grams of glycine betaine, such as from 100 to 500 milligrams per day. Preferably such patches are configured to hold sufficient betaine to release from about five to about 500 milligrams per day for seven days, such that a single patch may be worn for one week.

The optimum dose range, i.e., the range of doses with which the drug exhibits maximum therapeutic effect (and minimum adverse side effects for the other drug or therapeutic agent of the combination, when the patch is used in such a combination) can be determined empirically. The patch or other delivery system is configured and formulated to contain sufficient glycine betaine to release a dose within the optimum dose range for the desired period of time.

Another patch useful is a 4-layer composite defining at least two separate compartments. One compartment contains glycine betaine, and the other compartment contains a delivery substance that when mixed with glycine betaine permits the delivery of the glycine betaine transdermally. The patch has a backing layer sealed to a rate controlling membrane in a manner to create two chambers, a betaine-containing chamber and a delivery substance-containing chamber. An adhesive layer covers the rate controlling membrane and a release sheet covers the adhesive layer.

To form the device, a silanized polyester (or other suitable material treated with a releasing agent) approximately 75 microns thick, is used as a release sheet 34. The adhesive layer 32 is cast onto the release sheet, and may be, for example, polyisobutylene. The adhesive layer then is laminated to the rate controlling membrane 26, which may be about 100 microns thick. Ethylene-vinyl acetate may be employed for the control membrane. Next, the materials that will become the contents of the betaine-containing chamber and delivery substance-chamber are placed in separate areas on the rate controlling membrane. The material for the betaine-containing chamber may be betaine free base and the material for the delivery substance containing chamber may be an alcoholic or aqueous/alcoholic solution or water.

Finally, a suitable backing having a heat sealable coating on one surface is placed over the two areas which are to become the two chambers, and the device is heat sealed around the perimeter and between the two areas to form the two chambers. The heat seal between the two chambers should be less secure than the heat seal about the perimeter, so that the seal between the chambers will selectively burst under pressure applied by the user. In this manner, pressure may be applied to either one of the chambers to burst the seal between the chambers, thereby mixing the solution and the betaine and dissolving the glycine betaine (anhydrous). The betaine then is in a form that is capable of passing through the rate controlling membrane for delivery to the skin of the user. As with the patch disclosed in the first embodiment, the chambers may include enhancers or retarder for affecting uptake of the betaine across the skin.

Preferred forms of the foregoing patch are shown in greater detail in U.S. Pat. No. 4,917,676, issued Apr. 17, 1990 and entitled "User-Activated Transdermal Therapeutic System", the entire disclosure of which is incorporated herein by reference. Such patches should contain sufficient lobeline to release from about five to about 500 milligrams of glycine betaine per day (from 2 to 10 mg/kg), and such patches are suitable to provide individual, daily patches.

Example 32

In this example, parenteral (especially subcutaneous) solutions containing heparin and glycine betaine have been prepared. For example, the solutions of heparin sodium sold by CHOAY® (25000 IU/ml, aqueous solution), sold by LEO® and sold by ROCHE® were mixed with glycine betaine as a powder or as an aqueous solution, so as to prepare injectable solutions containing 25000 IU, 5000 IU and 2500 IU heparin (corresponding to 5 ml injectable solutions containing 5 mg/ml heparin and 100 mg/ml glycine betaine, injectable solutions containing 1 mg/ml heparin and 20 mg/ml glycine betaine, and injectable solutions containing 0.5 mg/ml heparin and 10 mg/ml glycine betaine).

Example 33

In said example oral formulations containing aspirin (acid acetylsalicylic) and glycine betaine have been prepared.
A) acid acetylsalicylic 500 mg+500 mg betaine+excipient
B) acid acetylsalicylic 300 mg+200 mg betaine+excipient
C) acid acetylsalicylic 300 mg+400 mg betaine+excipient
A, B and C being possibly coated with an enterosoluble or controlled release layer, such as tablet or pellet. Or A, B and C being possibly placed in a capsule with an enterosoluble or controlled release layer.
D) a syrup containing acid acetylsalicylic+betaine.

Example 34

This experiment utilized stock solutions of azure A, heparin, betaine, and a betaine-heparin combination in order to determine in vitro binding of betaine to Heparin. The stock solution of azure A was prepared at $4 \times 10^{-5}$ mol $L^{-1}$ by solubilizing 58.35 mg azure A in 50 ml of sterile injectable water. Next, 10 ml of this solution was diluted in 90 ml of sterile injectable water. The resulting solution was diluted again by taking 10 ml of this solution and diluting it in 90 ml of sterile injectable water. Finally, the resulting solution is filtered on Watman paper and aliquots of 4 ml are realized. The stock solution of Heparin was prepared by diluting the manufacturer-supplied stock solution (5000 UI/ml having ±150 UI/mg), (LEO Pharma, Ballerup, Denmark). One ml of this supplied solution was diluted in 499 ml of sterile injectable water in order to obtain a 10 UI/ml in final concentration. The betaine stock solution was prepared by diluting betaine in sterile injectable water in order to obtain a final concentration of 10 mg/ml. The Heparin-betaine combination stock solution was prepared by mixing 12 ml of the betaine stock solution prepared as noted above with 14.4 ml of the manufacturer-supplied Heparin stock solution (corresponding to 120 mg of betaine and 480 mg Heparin). This mixture was agitated for 2 minutes while mixing and then incubated for 10 minutes at 20° C. The final combination solution is then prepared by taking 1 ml of the solution after incubation and diluting it in 499 ml of sterile injectable water.

Each stock solution was then tested at six dilutions for its effect on heparin binding to azure A dye. The first dilution consisted of 0 µl solution, 400 µl water and 4 ml azure A solution. The second dilution consisted of 80 µl solution, 320 µl water and 4 ml azure A solution. The third dilution consisted of 160 µl solution, 240 µl water and 4 ml azure A solution. The fourth dilution consisted of 240 µl solution, 160 µl water and 4 ml azure A solution. The fifth dilution consisted of 320 µl solution, 80 µl water and 4 ml azure A solution. The sixth dilution consisted of 400 µl solution, 0 µl water and 4 ml azure A solution. Each dilution was then subjected to the azure A method which is a rapid and simple spectrophotometric method for determining heparin concentration following the formation of a soluble complex between heparin and azure A dye. Chemically, azure A is formed by 3 benzene nuclei and a terminal $N^+$. This soluble complex changes the typically blue color of the azure dye to purple. The principle of the test is based on the spectrophotometric absorption of the heparin/azure A dye complex at 632 nm. Heparin binding to azure A results in lowered absorbance and the solution gradually turns deeper purple as heparin concentration increases. In the presence of a substance which binds to heparin (e.g., protamine), azure A retains its blue color and absorbance remains constant. The results of this test are provided in the following table which illustrates that no significant change in the absorbance of azure A occurs when betaine is combined with heparin. However, Heparin alone has a significant effect on azure A absorption.

| Heparin UI/ml (reference) | 0 | 2 | 4 | 6 | 8 | 10 |
|---|---|---|---|---|---|---|
| Azure A + Heparin | 1.3075 | 1.0608 | 0.8399 | 0.5797 | 0.358 | 0.205 |
| Azure A + Heparin + Betaine | 1.341 | 1.296 | 1.281 | 1.2474 | 1.189 | 1.1221 |
| Azure A + Betaine | 1.301 | 1.241 | 1.213 | 1.1937 | 1.1612 | 1.154 |

Example 35

This example determined the effect of betaine on hemorrhage time in a heparinized rat. Forty male Wistar rats were purchased from Charles River, France and were acclimated for one week prior to testing. Each animal was weighed prior to testing (weights ranged from 225 to 275 g, mean weight=245 g) and the group of 40 rats was further divided into 4 groups of 10 rats each. One group acted as a control group and each rat in this group received a subcutaneous injection of saline 1 hour prior to testing. The second group received a 10 mg/kg subcutaneous injection of betaine 1 hour prior to testing. The third group received a 5 mg/kg subcutaneous injection of heparin 1 hour prior to testing and the last group received a subcutaneous injection consisting of 5 mg/kg heparin plus 10 mg/kg betaine 1 hour prior to testing. The rats were anesthetized by intramuscular injection of Nesdonal (200 mg/kg). The products were then injected subcutaneously in the abdomen one hour before the tail cut induced bleeding test. For the group receiving the combined heparin/betaine (group 4) injections, the heparin and betaine were injected using different syringes at different sites of administration (left and right sides of the abdomen) in order to avoid any direct reactions between the two substances.

The tail of the anaesthetized rat was dipped for 5 minutes in a water bath at 37° C. in order to induce a dilation of the peripheral vessels. The tail was then removed from the water bath and sectioned at 10-15 mm from the extremity. The chronometer was then started. The IHT is defined as the time, in seconds, between the tail section and the end of the hemorrhage or bleeding. The end of hemorrhage is defined as the moment when the last drop of blood is collected from the tail and when no other drop is observed during 180 seconds. The amount of blood was estimated by visual inspection. As shown in the following table, heparin treatment significantly prolongs the bleeding time. Betaine has no significant effect on bleeding time and combined use of betaine with heparin almost restored the bleeding time to normal, thereby indicating an antidote-like activity of betaine against heparin. By visual inspection, it was noted that the combined administration significantly reduced the volume of blood loss comparatively to the group receiving heparin.

| Rat # | Control | Betaine | Heparin | Combination |
|---|---|---|---|---|
| 1 | 110 | 162 | 767 | 218 |
| 2 | 110 | 173 | 680 | 176 |
| 3 | 156 | 194 | 734 | ** |
| 4 | 140 | 203 | 702 | 231 |
| 5 | 165 | 159 | ** | 229 |
| 6 | 180 | 142 | 663 | 155 |
| 7 | 106 | 123 | 735 | 278 |
| 8 | 156 | 197 | 567 | 192 |
| 9 | 97 | 166 | ** | 202 |
| 10 | 0 | 180 | 679 | 257 |
| Mean | 135.6 | 169.9 | 690.9 | 215.3 |
| S.D. | ±30.3 | ±25.2 | ±61.1 | ±38.7 |

* Rat died after anesthesia
** Not measured (no hemorrhage 3 minutes after cutting)

Example 36

This example investigated the effect of delayed betaine administration on active heparin-induced bleeding (antidote type administration) in a rat. Twelve male Wistar rats were purchased from Charles River, France and were acclimated for one week prior to testing. Each rat was weighed prior to testing (weights ranged from 245-280 g with a mean of 260 g) and the group of twelve was divided into 3 subgroups. Three rats were in the control group which received two saline injections, one at $T_0$, one at $T_0+45$ minutes. Three rats were in the betaine group which received one injection of heparin (5 mg/kg) at $T_0$. Six rats were in the antidote group which received a heparin injection (5 mg/kg) at $T_0$, and a betaine injection (10 mg/kg) at $T_0+45$ minutes. All three groups then had a bleeding test at $T_0+75$ minutes using the previously described methodology. However, at the end of the bleeding experiments, blood was sampled by intracardiac puncture on Na-citrate (3.8%, 1:10) and plasmas of the collected blood samples were kept at −20° C. for future biological assays. Chemical products were also identical.

The results of this example are provided in the table below which clearly shows that betaine administration drastically reduces the prolonged bleeding times induced by heparin administration. The delayed administration of betaine after heparin treatment was designed to mimic an antidote mode of administration and it nearly restored normal bleeding times. The volume of blood loss (again noted by visual inspection) was also significantly reduced in the antidote group compared to the heparin group.

| Rat # | Control NaCl 0.9% | Heparin 5 mg/kg | Heparin 5 mg + Betaine 10 mg |
|---|---|---|---|
| 1 | 121 | 658 | 143 |
| 2 | 98 | 597 | 132 |
| 3 | 115 | 533 | 212 |
| 4 | — | — | 115 |
| 5 | — | — | 136 |
| 6 | — | — | 128 |
| Mean | 111.33 | 596 | 144.33 |
| S.D. | ±11.93 | ±62.5 | ±34.44 |

Example 37

This example investigated the effect of delayed betaine administration in an antidote type administration inhibited the bleeding time and volume of blood loss induced by heparin treatment in a rat. Twenty male Wistar rats were purchased from Charles River, France and were acclimated for one week prior to the tests. Each rat was weighed prior to testing (weights ranged from 240-340 g with a mean weight of 275 g) and divided into 2 groups of 10 animals each. One group received an injection of heparin (5 mg/kg) at $T_0$. The second group received a heparin injection (5 mg/kg) at $T_0$, and a betaine injection (10 mg/kg) at $T_0$+30 minutes. Both groups were subjected to a bleeding test at $T_0$+60 minutes. The testing was performed using the previously described methodology with slight modifications. The tails were sectioned at 5-8 mm from the extremity. After transection, the proximal end of the tail was placed in a tube and blood was permitted to drip freely into a reservoir of 3.8% citrate solution (1 ml) until bleeding stopped. Blood loss volumes were then determined using a 1000 µl pipette. At the end of the experiments, before euthanasia, blood was sampled by intra-cardiac puncture on Na-citrate (3.8%, 1:9) and centrifuged at 4000 rpm/min for 20 minutes in order to obtain Poor Platelet Plasma (PPP). Fibrinogen, APTT, Prothrombin Time (Quick) and Anti-Xa activity were determined using an Automatic Coagulation Laboratory ACL 200 (Instrumentation Laboratory, France). Results of this testing are provided in the tables below which show that heparin induced bleeding times are shorter than those of previous tests. Betaine efficiency to reduce bleeding times was confirmed. The effect on the haemorrhage was also confirmed since there was a very significant reduction of the blood loss volumes when compared to the heparin group. The delayed administration of betaine after heparin treatment, designed to mimic an antidote mode of administration, almost restored the bleeding times and the volumes of blood loss in the 10 betaine-treated animals to normal.

In this study, APTT remained prolonged (up to 6×) despite betaine administration while Fibrinogen levels were slightly lowered versus heparin (−10%) and significantly versus the control (−23%). Remarkably, betaine administration normalized Prothrombin times in 8 out of 10 animals. In the same manner, betaine administration reduced AntiOXa activity by 74% in the antidote group compared to the heparin group. The Anti-Xa activity reduction occurred uniformly in all betaine-treated animals. The remaining residual Anti-Xa activity is quite interesting, showing that betaine retains a portion of heparin antithrombotic activity while completely suppressing its haemorrhagic side effects. Such uses will help reduce or avoid reocclusion in stents and arteries.

| | Heparin 5 mg/kg | | Heparin 5 mg + Betaine 10 mg | |
|---|---|---|---|---|
| Rat # | Bleeding Time (sec) | Volume µl | Bleeding Time (sec) | Volume µl |
| 1 | 290 | 1200 | 70 | 160 |
| 2 | 265 | 940 | 135 | 210 |
| 3 | 350 | 1140 | 220 | 300 |
| 4 | 300 | 1130 | 110 | 420 |
| 5 | 315 | 1300 | 138 | 410 |
| 6 | 275 | 1100 | 128 | 390 |
| 7 | 400 | 1650 | 115 | 350 |
| 8 | 345 | 1300 | 95 | 110 |
| 9 | 405 | 1800 | 120 | 225 |
| 10 | 370 | 1380 | 120 | 320 |
| Mean | 331.5 | 1294 | 125.1* | 289.5* |
| S.D. | ±50.24 | ±260.9 | ±38.88 | ±108.43 |

| | Heparin 5 mg/kg | | | Heparin 5 mg + Betaine 10 mg | | |
|---|---|---|---|---|---|---|
| Rat # | Fibrinogen g/L | APTT seconds | Quick seconds | Fibrinogen g/L | APTT seconds | Quick seconds |
| 1 | 2.15 | >180 | 52.3 | 1.66 | >180 | 23.2 |
| 2 | 1.77 | >180 | 57.4 | 1.67 | >180 | 23.4 |
| 3 | 2.1 | >180 | 55.3 | 1.95 | >180 | 25.6 |
| 4 | 1.53 | >180 | 66.2 | 1.86 | >180 | 57.8 |
| 5 | 1.62 | >180 | 66.0 | 1.44 | >180 | 23.2 |
| 6 | 2.0 | >180 | 59.6 | 1.46 | >180 | 22.3 |
| 7 | 1.55 | >180 | 64.6 | 1.51 | >180 | 21.0 |
| 8 | 1.67 | >180 | 67.2 | 1.51 | >180 | 22.1 |
| 9 | 1.57 | >180 | 62.2 | 1.67 | >180 | 21.8 |
| 10 | 2.2 | >180 | 59.9 | 1.54 | >180 | 67.4 |
| Mean | 1.82 | >180 | 61.07 | 1.63 | >180 | 30.78* |
| S.D. | ±0.27 | N.A. | ±5.04 | ±0.17 | N.A. | ±16.94 |

| | Anti-Xa IU/ml | |
|---|---|---|
| Rat # | Heparin 5 mg/ml | Heparin 5 mg + Betaine 10 mg |
| 1 | 1.35 | 0.35 |
| 2 | 1.38 | 0.34 |
| 3 | 1.37 | 0.36 |
| 4 | 1.38 | 0.31 |
| 5 | 1.37 | 0.39 |
| 6 | 1.34 | 0.37 |
| 7 | 1.41 | 0.33 |
| 8 | 1.39 | 0.33 |
| 9 | 1.35 | 0.38 |
| 10 | 1.39 | 0.40 |
| Mean | 1.37 | 0.36* |
| S.D. | ±0.02 | ±0.03 |

*P < 0.001 vs. heparin

CONCLUSION

Currently, heparin is used in angioplasty procedures to prevent thrombosis during or after the procedure. However, Protamine is avoided in this indication because it can cause thrombosis and blockade of the newly reopened artery. Without the use of a safe reversal agent, the patient must remain immobilized for hours while the heparin dissipates. This delay in restoring normal coagulation requires additional resources from the hospital, and leads to excessive bleeding in a significant number of patients. In regard to its particular profile, betaine can avoid stent and artery reocclusion, allowing an early discharge of patients. In clinical practice, betaine could be beneficial and useful to reverse heparin anticoagulation in other indications such as heart surgery (bypass), hip surgery, orthopadic surgery, prosthesis surgery, extracorporeal circulation and generally to reverse and/or to prevent heparin side effects such as bleeding, blood loss, thrombocytopenia, etc.

The combinations described in the examples may be useful in human clinics and treatments, particularly to natural haemorrhagic events linked to thrombosis and cardiovascular diseases or to events linked to side effects of drug administration following several diseases.

What I claim is:

1. A controlled release pharmaceutical system suitable for delivering after administration in a time-controlled manner to the bloodstream of a mammal comprising an effective amount of an active compound selected from the group consisting of a compound of the formula $(CH_3)_3N^+(CH_2)_nCOO^-$, with n equal to 1, pharmaceutically acceptable salts thereof, and mixtures thereof.

2. The system of claim 1, said system being selected from the group consisting of oral control led release preparations, oral controlled release devices, transdermal controlled release preparations, transdermal controlled release devices, and combinations thereof.

3. The system of claim 1 wherein said system comprises at least one electronic element selected from the group consisting of an electronic device and chip, said at least one element operable for controlling at least the releasing of the active compound.

4. The system of claim 1, said system controlling delivery of said compound for at least about 120 minutes.

5. A controlled release pharmaceutical system for achieving a goal selected from the group consisting of treating a condition, reducing the incidence of a condition, and reducing the severity of a condition, whereby said condition is selected from the group consisting of blood flow disturbances, thrombosis, thromboembolic disorders, and combinations thereof, said system being adapted for releasing in a time controlled manner for at least 120 minutes, after administration, a therapeutically effective amount of an active compound selected from the group consisting of a compound of the formula $(CH_3)_3N^+(CH_2)_nCOO^-$, with n equal to 1, pharmaceutically acceptable salts of said compound, and mixtures thereof.

6. The system of claim 5, said system being an oral controlled release pharmaceutical system.

7. The system of claim 5 wherein said system comprises at least one electronic element selected from the group consisting of an electronic device and chip, said element being operable for controlling the release of the active compound.

8. The system of claim 5, wherein the system is adapted for controlling the release of said active compound for at least for 180 minutes.

9. The system of claim 5, wherein the system is adapted for controlling the release of said active compound for at least for 240 minutes.

10. The system of claim 5, wherein the system is adapted for controlling the release of said active compound for at least for 360 minutes.

11. A controlled release pharmaceutical system tor releasing an effective therapeutic amount of a compound selected from the group consisting of a compound of the formula $(CH_3)_3N^+(CH_2)_nCOO^-$, with n equal to 1, pharmaceutically acceptable salts thereof, and mixtures thereof, wherein said system is adapted for controlling for at least 120 minutes the release of an effective amount of a compound of glycine betaine, pharmaceutically acceptable salts thereof, and mixtures thereof.

12. The system of claim 11, in which the system is adapted for controlling at least for 180 minutes the release of an effective amount of a compound selected from the group consisting of a compound of formula $(CH3)3N+(CH2)n COO^-$ with n being an integer of 1, pharmaceutically acceptable salts thereof, and mixtures thereof.

13. The system of claim 11, in which the system is adapted for controlling the release of an effective amount of a compound selected from the group consisting of a compound of formula $(CH3)3N+(CH2)n COO^-$ with n being an integer of 1, pharmaceutically acceptable salts thereof, and mixtures thereof for a time period of from about 240 minutes to 2160 minutes.

14. The system of claim 11 wherein said system comprises at least one electronic element selected from the group consisting of an electronic device and chip, said element being operable for controlling the release of the active compound.

15. A controlled release pharmaceutical system for achieving a goal selected from the group consisting of treating a condition, reducing the incidence of a condition, and reducing the severity of a condition, whereby said condition is selected from the group consisting of blood flaw disturbances, thrombosis, thromboembolic disorders, and combinations thereof, said system being adapted for releasing in a time controlled manner for at least 2160 minutes, after administration, a therapeutically effective amount at an active compound selected from the group consisting of a compound of the formula $(CH_3)_3N^+(CH_2)_nCOO^-$, with n equal to 1, pharmaceutically acceptable salts thereof, and mixtures thereof.

* * * * *

UNITED STATES PATENT AND TRADEMARK OFFICE
CERTIFICATE OF CORRECTION

PATENT NO. : 7,608,640 B2
APPLICATION NO. : 10/635048
DATED : October 27, 2009
INVENTOR(S) : Jallal Messadek Page 1 of 1

It is certified that error appears in the above-identified patent and that said Letters Patent is hereby corrected as shown below:

Col. 51;
Claim 2, line 15, the word "control led" should read --controlled--;

Col. 52;
Claim 15, line 38, the word "flaw" should read --flow--.

Signed and Sealed this

Twenty-ninth Day of December, 2009

David J. Kappos
*Director of the United States Patent and Trademark Office*